United States Patent [19]

Rothstein et al.

[11] Patent Number: 5,024,948
[45] Date of Patent: Jun. 18, 1991

[54] GENETIC SYSTEM FOR MICROMONOSPORA

[75] Inventors: David M. Rothstein, Rockland; Susan F. Love, Westchester; Ellen Z. Baum, Rockland, all of N.Y.

[73] Assignee: American Cyanamid Company, Stamford, Conn.

[21] Appl. No.: 22,455

[22] Filed: Mar. 6, 1987

Related U.S. Application Data

[63] Continuation-in-part of Ser. No. 787,066, Oct. 17, 1985, abandoned, and Ser. No. 672,031, Nov. 16, 1984, abandoned.

[51] Int. Cl.$^5$ .................. C12N 1/20; C12N 15/01; C12P 19/44
[52] U.S. Cl. .................. 435/252.1; 435/74; 435/169; 435/172.1; 435/172.3; 435/886
[58] Field of Search .................. 435/69.1, 71.1, 74, 435/169, 172.1, 172.3, 252.1, 867

[56] References Cited

PUBLICATIONS

Shier et al., 1969, *PNAS*, 63:198–204.
Serio et al., 1986, The Bacteria, vol. IX, Queener et al. (eds.), Academic Press, N.Y., 231–279.

*Primary Examiner*—Richard A. Schwartz
*Assistant Examiner*—Richard C. Peet
*Attorney, Agent, or Firm*—Alan M. Gordon

[57] ABSTRACT

A culture comprising the microorganism *Micromonospora echinospora* ssp. calichensis DR46 (ATCC-53591), which produces complementing factor, is described and disclosed.

1 Claim, 17 Drawing Sheets

DR 43 only

| | DR 210 | DR 1510 | DR 118 | DR 181 | DR 112 | DR 35 | DR 1014 | DR 201 | DR 156 | DR 91 | DR 123 | DR 58 | DR 1712 | DR 1316 | DR 46 | DR 43 | DR 194 |
|---|---|---|---|---|---|---|---|---|---|---|---|---|---|---|---|---|---|
| DR210 | | - | +| | - | - | - | - | - | - | - | - | - | - | - | +| | +| | - |
| BR1510 | - | | +| | - | - | - | - | - | - | - | - | - | - | - | - | +| | +| |
| DR118 | +| | +| | | + | + | + | + | + | + | + | - | - | - | +| | +| | + | + |
| DR181 | - | - | + | | - | - | - | - | - | - | - | - | + | - | + | +| | + | + |
| DR112 | - | - | + | - | | +| | - | - | - | - | - | - | - | + | + | + | + |
| DR35 | - | - | + | - | - | | - | - | - | - | - | - | + | +| | + | + | + |
| DR1014 | - | - | + | - | - | - | | - | - | - | - | - | + | +| | + | + | + |
| DR201 | - | - | +| | - | - | - | - | | - | - | - | - | + | + | + | + | + |
| DR156 | - | - | +| | - | - | - | - | - | | - | - | - | + | + | + | + | + |
| DR91 | - | - | + | - | - | - | - | - | - | | +| | + | + | + | + | +· | + |
| DR123 | - | - | + | - | - | - | - | - | - | +| | | + | + | + | + | + | + |
| DR58 | - | - | + | - | - | - | - | - | - | + | + | | +| | + | + | + | + |
| DR1712 | - | - | + | + | - | +| | +| | + | + | + | + | + | | +| | + | + | + |
| DR1316 | - | - | + | - | + | +| | + | + | + | + | + | + | +| | | + | + | + |
| DR46 | - | - | +| | +| | + | + | + | + | + | + | + | + | + | + | | - | + |
| DR43 | +| | +| | + | + | + | + | + | + | + | + | + | + | + | + | - | | + |
| DR194 | + | + | + | + | + | + | + | + | + | + | + | + | + | + | + | +| | |
| Complementation Groups: | 1 | | 2 | 3 | | | | | | 4 | 5 | 6 | 7 | 8 | 9 | 10 | |

DNA Sequence of _Micromonospora_ Promoters from pPP14

GATCTGCCGA TGTGTGCGCC GTCGTTGCGA GCACGGCTTG ATCCGCTCCC ACACCTGCGA GAAGTTCTCG

TTGGAGGGGT CGAGCAGGGA CCCCCACAGC TCCATCGAGA ACTGGCCCTT GGCGTCCAGC GGCTTGTAGA

P1a          P1b          P1c
TCGTTGACGT GCACCCTTGT GCACGGCACA CTGTCCCTGC CATGTGTGAC CTCGGTCCCC CGCGGGCACA
                                                                                           SstII

Ptk                                    P2
CAGGGAAGGC AGCGCCGGGA CAAGGTGTTG CACGATAGGT GAGCAACGAC CGAAGAGAGT GTTCATCGGT
          HpaII rbs
GACGACCAGA GGAGGAAGGC GATGACCCCG ACCCTCACGC GCGCCCGAGA CGGTGCTCCC CCAGCCGCCG
                    MET                                 AvaI ATGAACGGTG CGACCGCTGC AATGCTGCCG GCAAGCTCCG GATCC
                                             BamHI

FIG. 15

A. 73-31
1 2 3 4 5 6
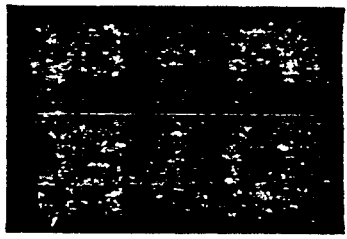
— P1
— P2
B. Minimal
1 2 3 4 5
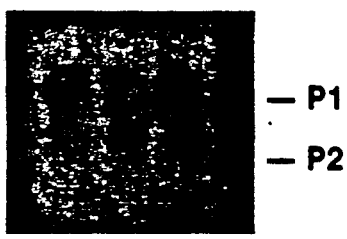
— P1
— P2
C. GER
1 2 3 4
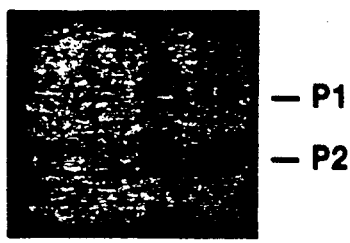
— P1
— P2
FIG. 17

GENETIC SYSTEM FOR MICROMONOSPORA

This is a continuation-in-part of copending application Ser. No. 06/787,066, filed Oct. 17, 1985, now abandoned, which is a continuation-in-part of co-pending application Ser. No. 06/672,031, filed Nov. 16, 1984, now abandoned.

BACKGROUND OF THE INVENTION

This invention concerns the genetic manipulation of a new Actinomycete *Micromonospora echinospora* ssp. calichensis, that produces the antibacterial and antitumor agents called LL-E33288 complex. Such antibiotic and anti-tumor agents are described in co-pending U.S. patent application Ser. No. 009,321, now U.S. Pat. No. 4,970,198, filed Jan. 30, 1987, which application is a continuation-in-part of co-pending application Ser. No. 787,066, filed Oct. 17, 1986, now abandoned, which is a continuation-in-part of application Ser. No. 672,031, filed Nov. 16, 1984 and now abandoned. Various derivative products of the LL-E33288 complex are described in co-pending applications Ser. Nos. 004,154 and 004,153, both filed Jan. 30, 1987. The disclosure of all such applications is herein incorporated by reference. The antibiotic and antitumor LL-E33288 complex is produced during the cultivation under controlled conditions of the new strain of *Micromonospora echinospora* ssp. calichensis. This microorganism is maintained in the culture collection of the Medical Research Division, American Cyanamid Company, Pearl River, N.Y. as culture number LL-E33288. A viable culture of this new microorganism has been deposited with the Culture Collection Laboratory, Northern Regional Research Center, U.S. Department of Agriculture, Peoria, Ill. on Aug. 9, 1984, and has been added to its permanent collection. It has been assigned by such depository the strain designation NRRL-15839. Access to such culture, during the pendency of application Ser. No. 009,321, now U.S. Pat. No. 4,970,198 shall be available to one determined by the Commissioner of Patents and Trademarks to be entitled thereto under 37 C.F.R. §1.14 and 35 U.S.C. §122, and all restrictions on availability to the public of such culture will be irrevocably removed upon grant of a patent on application Ser. No. 009,321, now U.S. Pat. No. 4,970,198.

THE INVENTION

We have developed effective methods to mutagenize strain NRRL-15839 and screen for derivative strains that produce no detectable product or an altered pattern of product. A protoplasting and regeneration regimen has been developed that has resulted in the transformation of strain NRRL-15839 with a plasmid. Furthermore, we have isolated and analyzed a DNA fragment from strain NRRL-15839 that contains promoter activity primarily at that stage in the life cycle of NRRL-15839 that the LL-E33288 complex is produced. By utilizing these genetic and biochemical advances, we can produce novel derivatives of strain NRRL-15839 that have improved characteristics (i.e., production of compounds with reduced toxicity), and we can enhance product yield. Because yields of the iodo-LL-E33288 complex were higher than the bromo-LL-E33288 complex, iodo-LL-E33288 complex was used exclusively in our work.

BRIEF DESCRIPTION OF THE DRAWINGS

FIG. 4 shows co-synthesis of LL-E33288 complex by blocked mutants of strain NRRL-15839, in that mutant strain DR43 was grown alone in 73-3I growth medium, or co-grown with other mutant derivatives, and the fermentation broths were tested for BIA activity.

FIG. 5 shows co-synthesis of LL-E33288 complex by 17 blocked mutants of strain NRRL-15839, with the following legend: (+), co-synthesis of LL-E33288 complex; (−), no detectable co-synthesis; (+/−), barely detectable production of LL-E33288 complex, complementation groups indicated by solid vertical lines.

FIG. 15 shows probable DNA sequence of the *Micromonospora* DNA fragment containing promoters for pPP14, in that the DNA sequence was determined by the method of Maxam and Gilbert and by Sanger and the location of promoters was determined by S1 nuclease protection of the same DNA fragments used for Maxam-Gilbert sequencing and electrophoresed on the same gel (the probable ribosome binding site [rbs] and initiator methionine codon [MET] are indicated).

FIG. 17 shows developmental expression of transcripts hybridizing to pPEC14, in that 10 μg of RNA isolated from *Micromonospora* cultures were analyzed by Northern blotting as described in FIG. 11; A: 73-3I medium, samples were taken at 17, 30, 41, 53, 70 and 92 hours (lanes 1-6); B: minimal medium, samples were taken at 30, 41, 53, 70 and 92 hours (lanes 1-5); and C: GER medium, samples were taken at 19, 28, 43 and 51 hours (lanes 1-4).

DETAILED DESCRIPTION OF THE INVENTION

Figure 1:
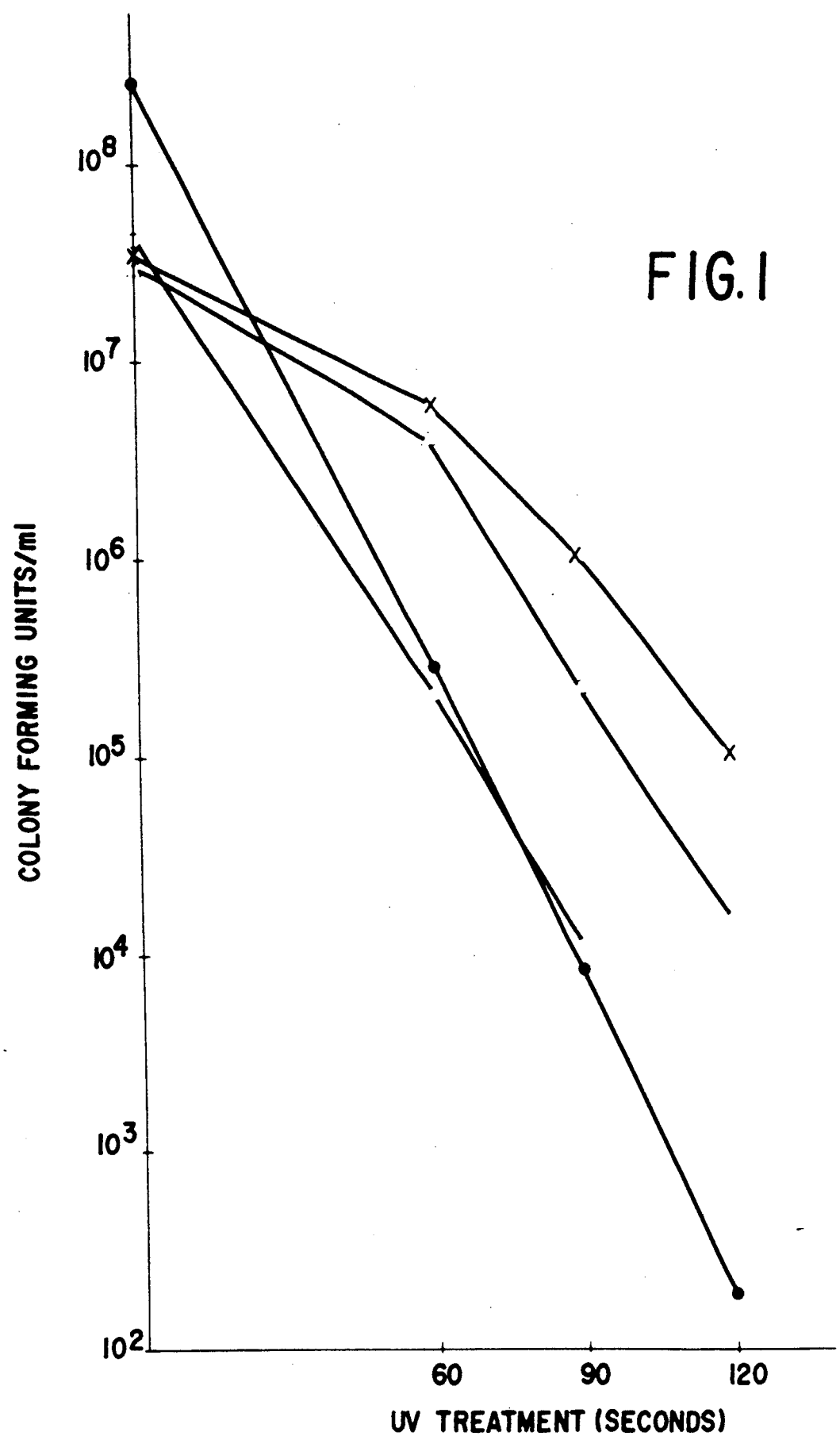
FIG. 1 shows survival of strain NRRL-15839 population as a function of ultraviolet light treatment, with the following legend: (●); −glycine in growth medium/+sonication prior to UV treatment, (); +glycine/+sonication, (X); −glycine/−sonication, (Δ); +glycine/−sonication.

Strain NRRL-15839 grows as a multi-cellular form called mycelia. The multi-cellular nature of growing cultures is a problem for mutagenesis; cells containing recessive mutations will not be detected in a cluster of wild type cells. One must resort to mutagenesis of spores, a non-growing unicellular form of the organism, or mutagenesis of growing cells that are then subsequently treated by protoplasting (digesting the cell wall) or sonicating (mechanically shearing the cell wall). By preparing protoplasts or sonicated mycelia, unicellular or near-unicellular genetic units are artificially generated. We describe effective protocols involving the mutagenesis of fragmented mycelia of strain NRRL-15839 with nitrosoguanidine and with ultra-violet light.

In order to transfer recombinant DNA into the producing organism, it was essential to develop a protoplasting-regeneration system, since protoplasts will generally take up exogenous DNA, whereas growing mycelia or non-growing spores will not. We have included all the details of these procedures, because protoplasting and regenerating appear to be delicate procedures. We also include details of the procedure for transferring genetic material between strains by protoplast fusion.

In order to clone genes into strain NRRL-15839, it is necessary to develop vectors that can replicate in the organism. A derivative of the plasmid pIJ486, a *Streptomyces* plasmid (J. M. Ward et al., Molecular and General Genetics, 1986, pp. 468-478), containing a promoter from strain NRRL-15839 for the kanamycin resistance gene, was used to transform strain NRRL-15839. We will also investigate the utility of other plasmids from *Micromonospora* and from *Streptomyces*. Endogenous plasmids were not observed in strain NRRL-15839. Large plasmids might not be detected, however.

The approach we have taken to manipulate the biosynthetic pathway is similar in some respects to the study of tylosin production in *Streptomyces fradiae*, or erythromycin production in *Streptomyces erythreus* [Seno, E. T. and C. R. Hutchinson. 1986. in "The Bacteria", Volume IX, (S. W. Queener, L. C. Day, editors; Academic Press Inc. New York) pp. 231-279]. Those studies involved the isolation of mutants blocked in antibiotic production, and the cloning of genes involved in antibiotic biosynthesis. Mutants that are blocked specifically in the production of LL-E33288 complex can be useful in establishing the biosynthetic pathway of the drug. Cloning genes involved in LL-E33288 complex biosynthesis can be of great value in increasing yields of drug, and in producing novel derivatives.

We have isolated mutants blocked in LL-E33288 complex production. Some pairs of blocked mutants can co-synthesize active product. One mutant of a pair secretes an intermediate that the other mutant can convert to LL-E33288 complex. By isolating and identifying intermediates made by the secreting blocked mutants, we can determine precursor components of the LL-E33288 complex molecules. By altering the component or intermediate that is fed to the converting strain, we can potentially generate novel derivatives of LL-E33288 complex by "bioconversion" (Shier, W. T., K. L. Jr. Rinehart, and D. Gottlieb. 1969. Proc. Nat. Acad. Sci. 63: 198-204). In the case of LL-E33288 complex, bioconversion is a more feasible way to produce novel products than chemical modification of LL-E33288 complex, due to the complicated and unstable structure of the various components of the LL-E33288 complex.

Another means of characterizing blocked mutants involves feeding cultures known components of the LL-E33288 complex. One such component is the pseudoaglycone, a degradation product of LL-E33288 complex that lacks the rhamnose moiety and an amino sugar. The loss of the amino sugar results in more than a 100-fold reduction in biological activity. The ability of blocked mutants to convert the pseudoaglycone to LL-E33288 complex indicates that they are incapable of carrying out a reaction essential for the formation of pseudoaglycone due to a genetic defect. By altering a fragment such as the pseudoaglycone it is again possible to produce novel products by bioconversion.

Blocked mutants can also serve as recipients of plasmid DNA in a transformation. It is possible to clone the biosynthetic genes by complementing blocked mutants with plasmid DNA carrying wild type DNA inserts. It is also possible to clone the biosynthetic genes into another organism. *Streptomyces lividans* is a well-characterized host which supports the replication of several useful cloning vectors [Hopwood, D. A., et. al. 1985. Genetic Manipulation of *Streptomyces*; A Laboratory Manual. (The John Innes Foundation, Norwich, England)]. We can prepare a library of *Micromonospora* DNA fragments ligated into plasmid DNA, transform *S. lividans*, and screen for transformants that synthesize LL-E33288 complex. It may prove impossible, however, to clone, and express, all the biosynthetic genes on a single DNA fragment. Production of LL-E33288 complex in a foreign host might also be lethal. It might be more feasible to clone a part of the pathway, by identifying genes coding for precursor molecules, that a blocked mutant converts to LL-E33288 complex. Other means of cloning biosynthetic genes into *S. lividans* or *E. coli* include selecting resistance to LL-E33288 complex, since drug resistance genes may be linked to biosynthetic genes. DNA probes from genes known to be involved in polyketiie biosynthesis (Malpartida, R. et. al. 1986. Abstr. Fifth Internat. Symp. on the Genet. of Industrial Microorganisms. p. 163) may also be used to identify genes with similar functions in strain NRRL-15839.

If the biosynthetic genes cannot be identified directly, we can screen for transcripts that are present only at the time of the life cycle when the LL-E33288 complex is synthesized; such transcripts may code for enzymes of the LL-E33288 complex biosynthetic pathway. A variation of this approach involves searching for promoters active only at the time of the biosynthesis of LL-E33288 complex, utilizing promoter probe plasmids. Finally it may be possible to identify a protein involved in LL-E33288 complex biosynthesis, and by sequencing the protein, we could design our own probe for screening DNA containing biosynthetic genes.

Cloning and expressing such genes presents the possibility of elucidating the pathway, and eventually of manipulating it to our advantage. By cloning and expressing a gene coding for the rate-limiting enzyme of the LL-E33288 complex biosynthetic pathway, for example, we could increase the yield of product. By transferring such genes to other microorganisms, it might be possible to produce novel forms of LL-E33288 complex, as has been reported for a derivative of actinorhodin within the genera *Streptomyces* (Hopwood, D. A., et. al. 1985. Nature 314: 642–644). It would be an important advance, if by cloning and transferring the LL-E33288 complex biosynthetic genes, an organism was able to produce a new form of drug that retained the anti-tumor function but was less toxic.

An important aspect of our plan is the ability to express genes at the proper time in the life cycle of the organism. It is possible, for example, that the expression of the LL-E33288 complex biosynthetic genes during the exponential phase might be lethal. One way to regulate expression of cloned genes is at the level of transcription, by utilizing a DNA sequence preceding a gene or genes that is only active as a promoter at the time that LL-E33288 complex is also made. The isolation of such promoters is therefore an important step in the establishment of an expression system in *Micromonospora* or *Streptomyces*.

A sensitive biological induction assay (BIA), involving the induction of $\beta$-galactosidase in response to DNA damage in an engineered strain of *E. coli*, and the thin layer chromatography system which separates different components of LL-E33288 complex, were utilized to detect LL-E33288 complex activity. These systems were essential for the screening and characterization of large numbers of mutagenized cells for those with altered properties.

Mutagenesis of Strain NRRL-15839

In order to isolate interesting mutants it was essential to mutagenize strain NRRL-15839. A common mutagenesis regimen for Actinomycetes is to treat spores with agents such as UV or nitrosoguanidine (Delic, V., D. A. Hopwood, and E. J. Friend. 1970. Mut. Res. 9: 167–182). We mutagenized a growing culture of mycelium, and not spores, with these agents. Generally mutagenesis with N-nitro-N-methyl-N-nitrosoguanidine (NTG), which acts most strongly at DNA replication forks, is enhanced in growing cells [Miller, J. H. 1972 Experiments in Molecular Genetics. (Cold Spring Harbor Laboratories, Cold Spring Harbor, N.Y.)]. To insure detection of mutants carrying recessive lesions, mycelia were sonicated (mechanically sheared) after mutagenesis and outgrowth, to provide single genetic units.

Culturing strain NRRL-15839 for Mutagenesis with NTG

The growth medium for mutagenesis was GER (Kim, K. S., and D. Y. Ryu. 1983. Enz. Mic. Technol. 5: 273–280), a rich medium supporting relatively rapid growth of NRRL-15839, containing 100 mM TES (N-tris[hydroxymethyl]methyl-2-aminoethane sulfonic acid) adjusted to pH 7.6. The buffer was added to maintain a relatively high pH on addition of NTG, which is a more effective mutagen near pH 8 (Delic, V., D. A. Hopwood, and E. J. Friend. 1970. Mut Res. 9: 167–182). During exponential phase, before orange pigment production and before mycelial clumping, cell density could be monitored with a Klett-Summerson colorimeter. The culture of strain NRRL-15839 was grown in a baffled Klett flask, since aeration improves growth, and the culture also contained 3 glass beads (4 mm) to break up mycelial masses.

A frozen seed culture of strain NRRL-15839 was added to a 25 ml culture of GER medium. Cells were incubated at 32° C. in a New Brunswick G76 shaking water bath set at 300 rpm. The initial inoculum was 14 Klett Units (green filter). After about twenty-eight hours the cells had grown to 118 Klett Units, or mid-log phase. Cells were harvested by centrifugation and resuspended in 10 ml containing 1 mg/ml NTG, 70% GER, and 100 mM TES at pH 7.6. The culture was incubated in the water bath, and aliquots of culture were centrifuged, washed 3 times with GER medium, and grown out by inoculating onto two GER plates, and one slant each of 65-15 medium[1] or yeast dextrose medium[2].

[1] 64-15 medium g/l: glucose 10 g dextrin 20 g yeast extract 5 g N$^Z$ Amine A 5 g; CaCO$_3$ (Mississippi Line) 1 agar 15 g pH 6.7-7.0 - made up with tap water [2] Yeast Dextrose Medium g/l yeast extract 10 g glucose 10 g agar 15 g Aph 6.8 - made up with tap water A 2 ml sample of the culture was removed at 2.8' and centrifuged in two microcentrifuge tubes. The sample was washed three times to remove NTG. Other samples were removed from the culture at 35', 91', and 164'.

Outgrowth was necessary to allow for expression of recessive mutations among the many cells of a mycelial clump. We inoculated the slants, since they support development of spores, which are single cells. Mutagenized spores were eventually used to screen for blocked mutants. Because spores took weeks to form, we also grew out the mutagenized samples on 2 GER plates as well. After several bacterial generations of growth on GER plates a mutant would presumably divide to form a small, genetically homogenous cluster within the mycelium. To obtain fragments of mycelia that were single genetic units, 1 ml of such mycelia were resuspended in GER broth in a microcentrifuge tube jacketed with ice, was sonicated for 14–25 seconds (MSE Soniprep 150 sonicator, amplitude 16 microns), and mycelia were reduced to 2-3 cell size, as determined by microscopic observation. Measurements of colony forming units were also helpful in optimizing the sonication time; sonication produces more units to form colonies, but also kills some fragments. The number of colony forming units as a function of sonication time was determined; the 14-25 second range was beyond the time maximum colony forming units.

Mycelia from the 2.8' and 35' samples were grown out for 4 days, and mycelial fragments were prepared and inoculated onto GER plates after diluting in 10.3% sucrose. The remainder of sonicated or unsonicated cells was diluted with glycerol to 20% and stored at −70° C. After 4 days of incubation at 30° C., clones were replicated with toothpicks onto minimal medium plates or GER plates. While obtaining valuable auxotrophic derivatives of strain NRRL-15839, we could also measure the mutagenesis frequency from these data. The minimal medium used initially was 73-3 with added phosphate, consisting of, per liter, 20 g sucrose, 1 g ammonium sulfate, 0.1 g FeSO$_4$.7H$_2$O, 0.2 g MgSO$_4$.7H$_2$O, 5 g CaCO$_3$ (Mississippi Lime), 0.05 g K$_2$HPO$_4$, and 20 g agar, adjusted to pH 7.5. We later found it was easier to test clones in a modified minimal medium (Aux medium), which substitutes 1/10 volume of TES 1M pH 7.5, and 7.37 g CaCl$_2$.2H$_2$O for Mississippi Lime, which confers an opaque grey color to the medium that obscures colonies. Our results were more definitive when Noble agar (Oxoid), which was free of nutrient contamination, was substituted for Difco agar.

For the third NTG time point, the outgrowing cells were allowed to incubate for 8 days, until colonies were a reasonable size. The 91' treatment with NTG resulted in a long recovery time for the culture. Since there was so much killing (see below), we replicated colonies directly from the plate of outgrown mycelia, and then collected and sonicated the plate culture as described above. It seemed likely that for at least some colonies, only one cell would have survived from the mycelial cluster that was plated. Only small discrete colonies were picked. It was possible that the population picked directly from the plate was enriched for mutants that did not grow as well as the wild type on GER plates, and therefore were smaller, and remained discrete during the 8 day incubation. After individual colonies were picked, the plate culture was harvested and sonicated as outlined above.

Results of NTG Mutagenesis

The frequency of mutagenesis with NTG generally correlates with killing [Miller, J. H. 1972. Experiments in Molecular Genetics. (Cold Spring Harbor Laboratories, Cold Spring Harbor, N.Y.)]. It was obvious that a dramatic increase in killing occurred with increasing time of NTG treatment. After 4 days of growth at 30° C., cells plated from the 2.8' sample formed a lawn on GER plates; about 5000 colonies grew on the plates containing the sample harvested after 35' NTG treatment, about 300 colonies from the 91' sample, and just 3 colonies for the 164' sample.

Preliminary analysis of the auxotrophic screen also suggested a very successful mutagenesis. After replicating and retesting clones on plates containing minimal or GER medium, mutants that failed to grow on minimal medium were tested on a series of plates in order to determine their nutritional requirement (Davis, R. W., D. Botstein, and J. R. Roth. 1980. Advanced Bacterial Genetics, Cold Spring Harbor Laboratory, Cold Spring Harbor, N.Y.). Auxotrophs from the various time points are listed below.

| Time of NTG treatment | Proportion of mutants | | Nutritional requirements (number obtained in parenthesis) |
| --- | --- | --- | --- |
| 2.8' | 4/349 | 1.1% | aromatic amino acids (Aro) (2), tryptophan (1), histidine (1) |
| 35' | 55/765 | 7.2% | Aro (44), uracil + arginine (4), adenine (1), tryptophan (1), undefined (5) |
| 91' | 94/400 | 23.5% | Aro (66), tryptophan (9), undefined (2), untested (15) |
| 91'[3] | 12/100 | 12.0% | Aro (11), lysine (1) |

[3] replicated directly, prior to sonication

Results of the mutagenesis showed a high mutation frequency which increased with time of NTG treatment. We could define most mutants, consistent with the selection of single mutations. Several useful auxotrophic strains were obtained, consisting of six classes. We did, however, observe a pronounced clustering of mutations. The more highly mutagenized, the narrower was the spectrum of mutations observed. Mutations affecting biosynthesis of the aromatic amino acids (Aro) were by far the predominant class. It is known that NTG can have mutational "hotspots", especially near the origin of DNA replication (Guerola, N., J. L. and E. Cerda-Olmedo. 1971. Nature 230: 122). We were concerned that the high proportion of Aro mutants reflected such as skewing in the distribution of mutations. We therefore used ultraviolet light (UV) as a second way to induce genetic lesions.

Mutagenesis with UV Light

The protocol was designed to minimize the shielding of cells from UV light, which would attenuate its mutagenic effect. Cells were resuspended in a clear solution that was shallow enough (depth less than 2 mm) to allow all cells to be exposed. To overcome shading of cells by other cells within a mycelium, we sonicated to break up mycelial clumps to the size of 2-3 cells. The alternatives were mutagenesis of spores Hopwood, D. A., et. al. 1985. Genetic Manipulation of *Streptomyces;* A Laboratory Manual. (The John Innes Foundation, Norwich, England); Delic, V., D. A. Hopwood, and E. J. Friend. 1970. Mut. Res. 9: 167-182], or of protoplasts. After mutagenesis, the culture was grown out for several cell divisions to allow mutants containing recessive lesions to form small cell clusters within mycelia. The outgrown culture was again sonicated to produce single genetic units, and tested for auxotrophy.

About $5 \times 10^9$ cells from a growing culture of strain NRRL-15839 in GER medium were washed in 10.3% sucrose, sonicated as described above, resuspended in 10 ml of 20% glycerol in a Petri dish, and exposed to $2.4 j/m^2/sec$ of UV light (256 nm). At 60, 90, and 120 seconds, 2.8 ml of cells were taken from the cell suspension, and cells were diluted and inoculated onto GER plates for outgrowth. The unused portion of UV-treated cells were stored at $-70°$ C. Other variations of the protocol included UV mutagenesis of unsonicated cells. Cells grown in GER medium containing 0.15% glycine were also treated with UV light, since cells growing in the presence of glycine were observed to contain smaller mycelia (perhaps because of the effect of glycine on the cell wall). After four days colony forming units were determined, as shown below.

| Sonication prior to UV: | Growth Medium: | | | |
|---|---|---|---|---|
| | GER | | GER + glycine | |
| | yes | no | yes | no |
| Colony Forming Units/ml | | | | |
| 0 UV | $2.5 \times 10^8$ | $3.5 \times 10^7$ | $4 \times 10^7$ | $3 \times 10^7$ |
| 60 sec UV | $2.9 \times 10^5$ | $4 \times 10^6$ | $2 \times 10^5$ | $4 \times 10^6$ |
| 90 sec UV | $8 \times 10^3$ | $1 \times 10^6$ | $1 \times 10^4$ | $2.3 \times 10^5$ |
| 120 sec UV | $2 \times 10^2$ | $1 \times 10^5$ | $1.6 \times 10^4$ | $1.5 \times 10^4$ |

A survival curve is shown in FIG. 1. For sonicated cells a logarithmic relationship was observed for survival as a function of the time of exposure to UV light, and killing was very extensive. For mycelia that were not sonicated prior to treatment with UV light, killing was less extensive, probably because of shading. For early time points survival of unsonicated mycelia may be over estimated; if even one cell within a mycelial cluster survives, then no killing is detected.

Because killing by UV light is often correlated with mutagenesis [Miller, J. H. 1972. Experiments in Molecular Genetics. (Cold Spring Harbor Laboratories, Cold Spring Harbor, N.Y.)], these populations were likely to contain mutants. Plate cultures for each regimen were harvested by scraping outgrown mycelia into GER medium. For cell suspensions that were sonicated prior to UV treatment, cells exposed to UV for 90 seconds were used; unfragmented mycelia treated with UV for 120 seconds were harvested. In all cases outgrown mycelia were fragmented by sonication. After four days of incubation on GER plates, colonies were screened for growth by toothpicking onto minimal agar plates and GER plates. The following proportions of auxotrophs were observed for the four mutagenized cultures: growth in GER and no sonication prior to UV treatment, 0/370 (less than 0.3% auxotrophs), growth in GER with sonication, 3/285 (1% auxotrophs), growth in GER+glycine and no sonication 0/388 (less than 0.3% auxotrophs), and growth in GER+glycine with sonication, 1/312 (0.3% auxotrophs).

Since sonication enhanced both killing and mutagenesis by UV light, we screened the metagenized culture of cells grown in GER, and sonicated prior to treatment with UV. We observed a total of 38 auxotrophs of 1820 screened, or 2.1%. Auxogeny revealed 33 cysteine or methionine requirers, 3 histidine requirers, 1 threonine requirer, and undefined mutant. Again we observed clustering of mutants, this time requirers of organic sulfur (cysteine or methionine).

Summary of Auxotrophs and Pigment Mutants

We grew up auxotrophs representing every class in liquid Aux medium with and without supplements and confirmed all nutritional requirements. Fresh colonies from GER plates were washed and resuspended in 5 ml of broth and incubated at 28° C., using a roller drum for good aeration. Taken together the two mutagenesis procedures resulted in 8 different classes of nutritional requirers. The only overlap of auxotrophs between UV- and NTG- induced mutants was histidine requirers.

The uses of auxotrophs include the following. Two classes (Aro, and uracil-arginine requirers) were used in a protoplast fusion experiment described below. Auxotrophic alleles are of value in assuring that a given strain or colony is marked, and distinguishable from contaminants. It may prove useful to clone a wild-type gene that compensates for an auxotrophic mutation on a plasmid; the uptake and maintenance of the plasmid could be selected for by growing transformants on minimal medium. The mutants requiring organic sulfur may prove useful for labeling the LL-E33288 complex, because each LL-E33288 complex component contains 4 sulfur atoms.

A broad spectrum of mutants would have suggested that any non-lethal mutant could be found in our mutagenized populations. It is unclear why certain auxotrophs predominated, such as Aro mutants for NTG-treated cells. The aro region could be a mutational hotspot site for NTG. It is also possible that aro mutations confer a selective advantage during NTG treatment or outgrowth. Alternatively the aro region might be highly mutagenic in strain NRRL-15839, as the argG locus is in *Streptomyces* (J. Altenbuchner et al., 1984, Molecular and General Genetics, 195 pp 134-138). It is also possible that we were counterselecting for classes of auxotrophs. At least for Aro, tryptophan, histidine, threonine, and lysine auxotrophs, cells grew up faster in Aux medium containing only essential supplements, as opposed to Aux medium containing all supplements. Perhaps nonessential amino acids interfere with the uptake of the essential amino acid, inhibiting growth. The threonine and histidine requirers grew markedly poorly on GER medium compared to the wild type. In any case it seemed reasonable to test both the NTG- and UV-treated cultures for other desirable mutants, such as blocked mutants.

One other class of mutants that was observed from NTG-treated cells were pigment mutants. Wild type colonies of strain NRRL-15839 make an orange color after incubation for several days on GER plates. Several clones were observed from NTG-treated cells that no longer produced orange pigment. Some mutant colonies were white and some yellow. Our initial interest in such mutants stemmed from the observation that pigment production in wild type cultures occurred at about the time that LL-E33288 complex was produced. Further experimentation showed, however, that there was no intimate connection between the ability to make pigment and to produce drug, since these pigment mutants maintained the capacity to produce LL-E33288 complex. These mutants could be useful as recipients in a plasmid transformation that restored the capacity to make pigment, due to insertion of wild type *Micromonospora* DNA. Since pigment production is temporally controlled, the isolation of the regulatory sites from such genes could be useful in establishing a regulated expression system.

Isolation of Mutants Blocked in LL-E33288 Complex Production

In order to isolate blocked mutants, we had to miniaturize the fermentation conditions so that many clones could be quickly screened. Colonies were inoculated directly into 1.5 ml of 73-3I medium[4], using 24 well plates (Corning). Each well contained one glass bead to prevent clumping. For a quick screen, 3 or 10 μl of culture broth was spotted on a BIA plate, which had been inoculated with the *E. coli* tester strain. BIA-active material was identified from wild type cultures within three days. Because inocula were not uniform, cultures were incubated for a full week to avoid artifacts.

| [4]73-3I Medium | |
|---|---|
| | g/l |
| Sucrose | 20.0 |
| $FeSO_4.7H_2O$ | 0.1 |
| $MgSO_4.7H_2O$ | 0.2 |
| $CaCO_3$ (Miss. Lime) | 2.5 |
| Marcor Peptone | 2.0 |
| Molasses | 5.0 |
| KI | 0.1 |
| made up with tap water | |

In order to observe specific components of LL-E33288 complex, the extraction process also had to be streamlined. For those cultures that were positive for BIA-active material by the quick screen, 0.8 ml of culture was mixed with 325 μl of an acetone/ethyl acetate mix (8 volumes acetone/5 volumes ethyl acetate) in a microcentrifuge tube, and vortexed well for 2′ using a Multi-tube Vortexer (Scientific Manufacturing Industries). After centrifuging, 10 μl was spotted onto a TLC (Kieselgel 60 F254 from EM Science), and chromatographed as described, except just for 20′. Enough active material could be extracted within the small volume of the organic phase to detect LL-E33288 complex components, after TLC, on a BIA plate. To store the mutants, a 60 μl sample of all cultures was added to 40 μl of 50% glycerol, in a well of a 96 well plate, and frozen at −70° C.

Figure 2:
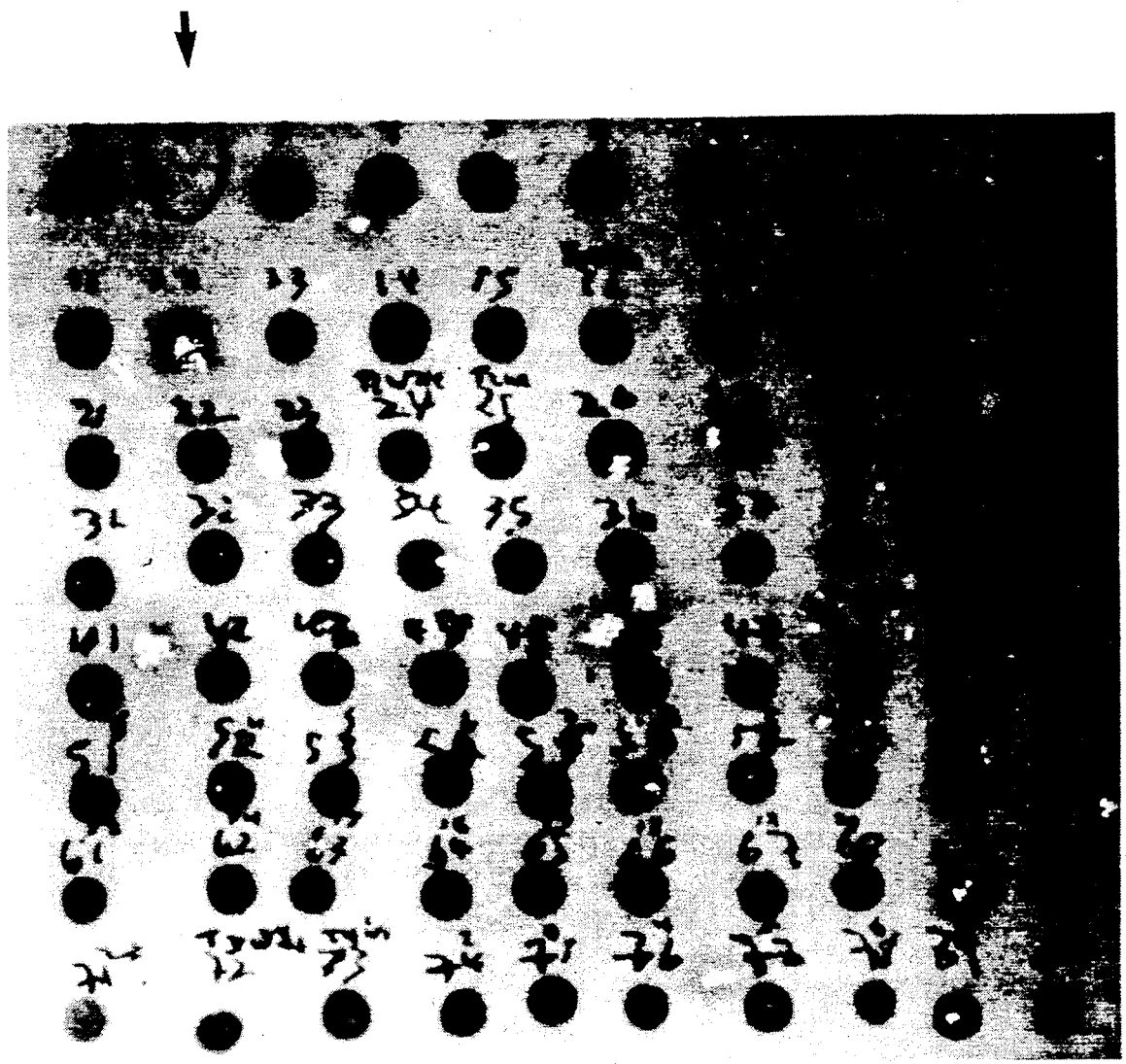
FIG. 2 shows screening for nonproducing mutants, in that clones were inoculated in 1.5 ml of 73-3I growth medium and incubated for 1 week at 28° C., ten μl of each fermentation broth was spotted on a BIA plate, and the arrow points to a spot of a n<,nonproducing fermentation.

By screening clones for BIA activity, several potentially interesting nonproducing derivatives were obtained (FIG. 2). We wanted quickly to eliminate mutants that failed to produce LL-E33288 complex for extraneous reasons related to poor growth or pleiotropic mutations affecting secondary metabolism. We had already determined that orange pigment production was not intimately associated with LL-E33288 complex production, since pigment mutants made BIA-active product. Pigment production occurs in the wild type, however, concurrently with LL-E33288 complex. Those nonproducers that failed to grow to confluence, and/or failed to make orange pigment, were discarded. We isolated 10 nonproducing mutants that grew to confluence of 240 clones tested, derived from cells mutagenized with NTG for 35′ and sonicated. Six nonproducers were obtained from 240 clones tested, of cells mutagenized with NTG for 35′ and then sporulated, and 1 of 480 mutagenized with UV.

Figure 3:
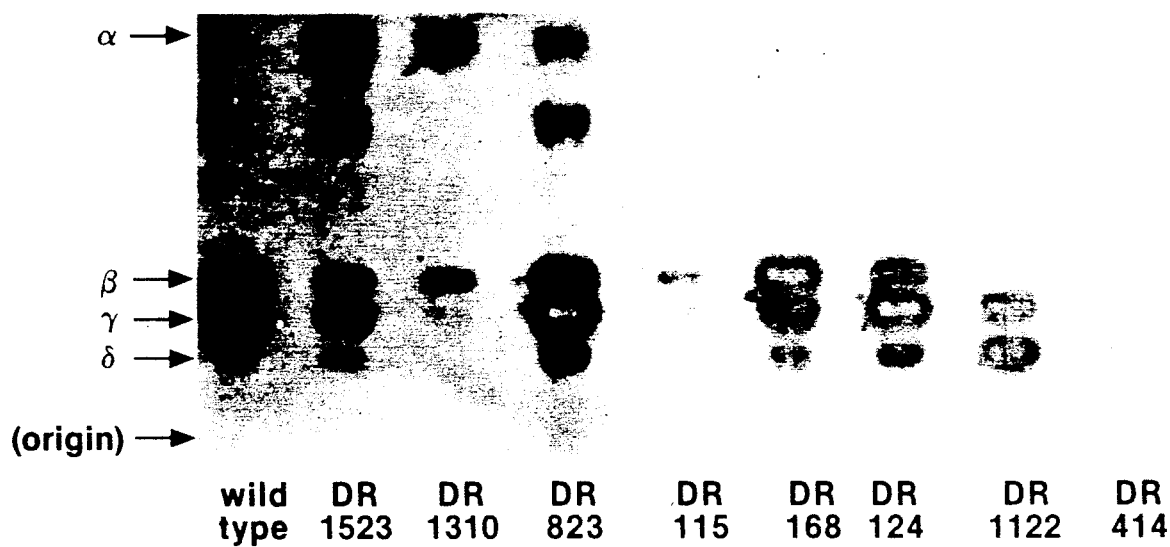
FIG. 3 shows TLC and bio-autography of LL-E33288 complex produced by mutant derivatives of strain NRRL-15839.

Isolation of Mutants Producing an Altered Profile of LL-E33288 Complex Components The clones that produced BIA-active material were tested for LL-E33288 complex components by screening with TLC plates as outlined above. A TLC of a collection of mutants displaying an altered profile of LL-E33288 complex components is shown in FIG. 3. One mutant of strain NRRL-15839, called DR414, produces only one visible component co-migrating with the delta component from NRRL-15839. Another (DR1122) makes no beta component, which is the major component produced by strain NRRL-15839. Several (DR823, DR1310, DR1523) produce considerably more of faster migrating components than strain NRRL-15839. Four of these mutants are from NTG mutagenized cells that were sonicated after outgrowth, and the others from NTG mutagenized cells that were sporulated. We do not know whether these mutants produce novel derivatives of LL-E33288 complex, or make more of minor components that are also produced by strain NRRL-15839. If novel products are made by one or more mutants, then they could exhibit the kinds of characteristics (i.e. reduced toxicity) that would be very valuable. If they emphasize a particular component, such as delta for DR414, then they could prove useful in isolating this component.

Co-Synthesis of LL-E33288 Complex by Blocked Mutants

In order to demonstrate that a given mutant is blocked specifically in the LL-E33283 complex pathway, we assayed for product from mixed cultures. If two mutants could co-synthesize BIA-active material, then one mutant might provide a precursor that overcomes the defect of the second mutant. The diagram below is an example of a linear biosynthetic pathway:

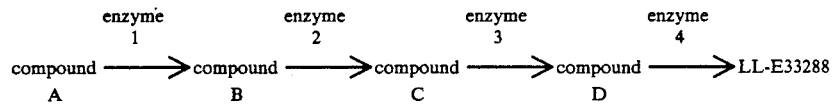

Mutant DR46 might contain a defect in enzyme 2, and therefore fail to make active product. Suppose mutant DR43 contains a lesion in enzyme 1, an earlier step in the pathway. If strain DR46 produces intermediate B and secretes it into the growth medium, then strain DR43 might take up intermediate B and convert it to the final product, since DR43 contains enzymes 2, 3 and 4. By taking up compound B, DR43 bypasses its genetically defective gene product (enzyme 1).

The co-synthesis of BIA-active material by two mutant strains does not unequivocally demonstrate that each is blocked specifically in the LL-E33288 complex biosynthetic pathway. The mutants might actually contain nutritional deficiencies, for example, although most classes of auxotrophs make at least some product. (Only the adenine requirer and two classes of undefined mutants failed to produce BIA-active material of auxotrophs tested.) Another possibility is that one mutant fails to produce an essential sugar component of LL-E33288 complex. Such a defect would not show up as an auxotroph, but the defect could be alleviated by supplementing the growth medium with the sugar, rather than a compound specific to LL-E33288 complex. However, some mutants that are blocked specifically in the LL-E33288 complex pathway could fail to co-synthesize if they produce an unstable intermediate, or one that is not secreted or taken up.

We prepared inocula of each mutant by growing to saturation in GER medium, washing, and storing 5x concentrated culture in 20% glycerol at $-70°$ C. Then 5 $\mu$l of a given mutant were inoculated with 5 $\mu$l of another mutant, or 10 $\mu$l of a single mutant were inoculated into a well of 73-3I production medium in a 24 well plate. After one week cultures were spotted on BIA plates to detect LL-E33288 complex. An example of the co-synthesis of mutant DR43 is shown in FIG. 4. Whereas strain DR43 grown alone produces no BIA-active material, strain DR43 grown with several other mutant strains co-synthesized the LL-E33288 complex. A summary of the co-synthesis experiments is shown in FIG. 5. If two mutants co-synthesize, they are in distinct complementation groups; if they fail to co-synthesize, they may contain mutations affecting the same step in the pathway, or they could affect different functions, but fail to complement for the reasons given above.

The results of the co-synthesis showed that every nonproducer co-synthesized with at least 2 other mutants. Among the 17 mutants, we observed 11 complementation groups, based on the ability of mutants to co-synthesize, or based on a distinct pattern of co-synthesis with other mutants. One would expect, for such complicated molecules as present in LL-E33288 complex, that at least 40 biochemical steps would be involved.

Eventually we focused on interesting mutants. Some mutants proved to be leaky (DR91, DR58, DR112, DR194), and were not followed up because the small amount of active material produced by a leaky mutant might have interfered with subsequent experiments. In addition DR172 was not examined extensively because it had a nutritional requirement. Four strains were eliminated from immediate attention because they were of the same large complementation group, and we could not distinguish them easily.

Co-synthesis experiments in liquid culture cannot determine which mutant of a pair is secreting a compound, and which mutant is converting the compound to active product. In order to distinguish secreters and converters, cells were spotted on production medium in a semi-solid matrix, containing 0.5% low melt agarose (Seakem), so that maximum diffusion was permitted. Mutant cultures were spotted in pairs adjacent to each other. After one week of growth, each spot was harvested by peeling colonies off of the agar surface, and cells were treated with 20 $\mu$l of acetone-ethyl acetate (1/1 vol/vol). Three $\mu$l of the ethyl acetate phase was spotted onto a BIA plate. The mutant of a pair that produced the stronger signal was assumed to be the converter and the other strain the secreter. Since LL-E33288 diffuses in the agar, results are not definitive. Not all pairs on plates co-synthesized detectable material. Still we were able to make preliminary determinations of the following pairs of mutants: mutants:

| Secreter | Converter |
|---|---|
| DR210 | DR43 |
| DR118 | DR43 |
| DR58 | DR43 |
| DR1712 | DR43 |
| DR1316 | DR43 |
| DR46 | DR43 |
| DR43 | DR1510 |
| DR123 | DR46 |
| DR58 | DR46 |
| DR1712 | DR46 |
| DR1316 | DR46 |
| DR123 | DR1316 |
| DR118 | DR1510 |

Assuming that converting strains are blocked earlier than secreting strains, a genetic order can be established for the biosynthetic pathway. A tentative map of the LL-E33288 complex pathway, ordering mutants according to their block, follows.

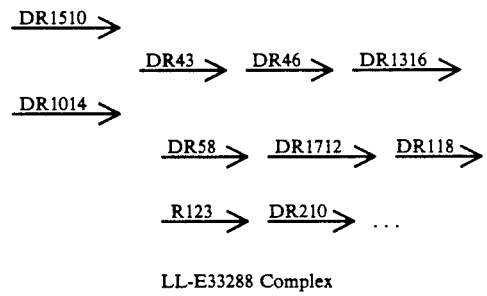

LL-E33288 Complex

It became clear that mutant DP43 was a particularly good candidate to examine in detail. It co-synthesized with several different mutants, and experiments suggested that mutant DR43 was usually the converting strain. Therefore DR43 probably contains a lesion early in the pathway. The clearest delineation on plates was observed when DR43 (converter and DR46 (secreter) were co-grown.

A viable culture of mutant strain DR46 is maintained by the Medical Research Division American Cyanamid Company, Pearl River, N.Y. Additionally, a viable culture of mutant strain DR46 has been deposited with the American Type Culture Collection, 12301 Parklawn Drive, Rockville, Md. 20852 on Mar. 6, 1987, and has been added to its permanent collection. It has been assigned by such depository the strain designation ATCC-53591. Access to such culture, during the pendency of the instant application, shall be available to one determined by the Commissioner of Patents and Trademarks to be entitled thereto, under 37 C.F.R. 1.14 and 35 U.S.C. 122, and all restrictions on availability to the public of such culture will be irrevocably removed upon grant of a patent on the instant application.

Characterization of an Intermediate of LL-E33288 Complex Biosynthesis

Since mutant DR46 appeared to secrete an intermediate that mutant DR43 converted to BIA-active material, it was likely that at least some of the intermediate would be found in the supernatant of a culture of strain DR46. Then it would be possible to add back a cell-free supplement from strain DR46, allowing strain DR43 to produce active material. The success of such an experiment depends on the stability of the intermediate; if it is very unstable, then it may be necessary to grow strains DR43 and DR46 together to detect co-synthesis.

The putative intermediate might be found in the supernatant of a culture of strain DR46. Alternatively it might be predominantly inside of cells. We decided to supplement cultures of strain DR43 with different components of a strain DR46 culture in order to distinguish these possibilities. Because the time of secretion of the intermediate was not known, a mixture of five timed cultures of strain DR46 was prepared. The five 50 ml cultures were harvested after 1, 2, 3, 4 and 6 days of growth in 73-3I production medium. A mixture of supernatants and cell pellets was prepared. The cell pellet mixture was resuspended in 10 ml H$_2$O and sonicated for a total of 17' (15 seconds sonicating per minute, jacketed with ice, MSE Soniprep 150, 15 microns). Few cells remained intact. The sonicate was centrifuged to remove debris, and filter-sterilized. The precipitate was extracted with ethyl acetate, since LL-E33288 complex is mostly found in an ethyl acetate extraction, and is not very soluble in water. The ethyl acetate extract was dried and resuspended in ethanol.

Strain DR43 cultures were inoculated in 24 well plates, and after 1, 2 or 3 days the components of the strain DR46 mixed culture were added. After 4 days of growth, BIA-activity was tested by spotting cultures. (To maintain a constant volume when large volumes of the strain DR46 culture supernatant were added to a well, an equal volume of the strain DR43 culture was centrifuged, and the pellet was added back.) The supernatant of the culture of strain DR46 contained the putative intermediate ("complementing factor"). 150 $\mu$l of supernatant of strain DR46 contained sufficient complementing material to be detected, following conversion by strain DR43, to BIA-active material. 750 $\mu$l of supernatant from strain DR46 cultures supplemented strain DR43 at least as well as the co-synthesis of DR43 and DR46. The equivalent of 1.7 ml of cell sonicate supplemented about as well as 150 $\mu$l of supernatant, indicating that the intermediate was predominantly in the culture supernatant, and not inside the cell. The ethyl acetate extract from the equivalent of 8 ml of strain DR46 cells (10 $\mu$l of concentrated extract) did not detectably supplement.

Figure 6:
FIG. 6 shows time course of complementing factor produced by a culture of mutant strain DR46, in that sterile supernatant of a 73-3I culture of strain DR46 was prepared at the times indicated, and 1.3 ml (days 1 and 2) or 130 μl (days 3, 4 and 6) of such supernatant was added back to a 73-3I culture of strain DR43, and conversion of complementing factor to LL-E33288 complex was measured by spotting 3 μl samples of the DR43 culture on a BIA plate.

Since the complementing factor produced by strain DR46 was found primarily in the culture supernatant, we concentrated our efforts there. 1.3 ml of supernatant from strain DR46 cultures incubated 1 or 2 days, and 130 $\mu$l of supernatant from strain DR46 cultures incubated 3, 4 and 6 days, were added back to cultures of strain DR43 after two days of growth in wells. On day 4 samples were spotted on a BIA plate to determine if complementing factor was in the supernatant (FIG. 6). In order to observe the BIA response accurately, 3 $\mu$l samples of culture undiluted, diluted ½, and diluted 1/10 were applied to the BIA plate. No complementing and 130 $\mu$l of supernatant from strain DR46 cultures incubated factor was detected from the strain DR46 supernatant from day 1, and a barely detectable amount of complementing factor by day 2. The concentration of complementing factor in the supernatant increased substantially by day 3, and peaked by day 4. The appearance of complementing factor in the supernatant of the strain DR46 culture parallels the appearance of LL-E33288 complex made in the wild type. The complementing complementing factor is synthesized in the life cycle after the end of growth, as is the case for LL-E33288 complex in the wild type (see below). The temporal coincidence is consistent with the conception that complementing factor is a specific precursor of LL-E33288 complex, and not, for example, a sugar that is synthesized during growth and stationary phase. Furthermore, the supernatant from S. lividans TK54 grown in 73-3I medium (with added histidine and leucine) does not provide complementing factor to strain DR43.

The chemical properties of complementing factor also indicate that it is not a simple sugar, but rather a precursor with hydrophobic and hydrophilic domains. The complementing factor did not partition into the organic phase after ethyl acetate addition, but about ½ the complementing factor entered the secondary butanol phase when an equal volume was added to supernatant. About ⅓ of the complementing factor was found in n-butanol when it was mixed with supernatant.

We have developed a process that an be used to isolate complementing factor from large cultures of strain DR46. The complementing factor adsorbs to ambersorb XAD-2 beads (Rohm and Haas). It is eluted almost completely with 80% methanol. The process has been scaled up to enable the isolation of complementing factor from a 300 l fermenter. The culture of strain DR46 is filtered, and the supernatant of the fermentation is applied to a 30 l column of XAD-2 beads. Most of the complementing factor is retained on the column, and then eluted with a 50% water-methanol mix. After lyophilization, complementing factor has been further purified by reverse-phase column chromatography, using an LH20 or a C18 matrix.

Figure 7:
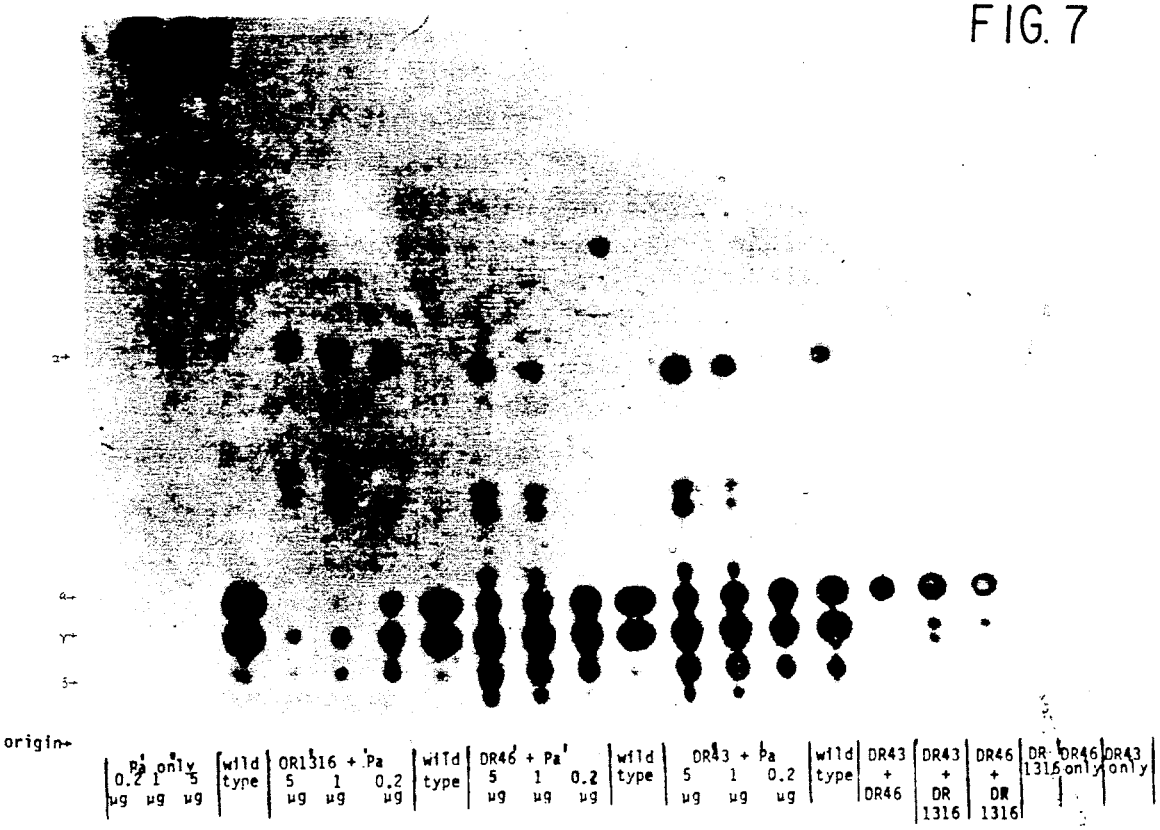
FIG. 7 shows conversion of the pseudoaglycone fragment of LL-E33288 complex by blocked mutants, to LL-E33288 complex components, in that pseudoaglycone (Pa) was added back to the indicated strains after 2 days of incubation in 73-3I growth medium, after 1 additional day LL-E33288 complex was extracted, components were separated by TLC, and assayed by bio-autography (positions of Pa and various components of the LL-E33288 complex are indicated).

When strains DR43 and DR46 were co-grown, only the beta component of LL-E33288 complex was made (see FIG. 7). The same result was observed when a culture of strain DR43 was supplemented with complementing factor. Based on these observations and the chemical properties of complementing factor, we suspect that complementing factor contains sugars, as well as a benzene ring (contributing a hydrophobic domain).

Conversion of Pseudoaglycone to LL-E33288 complex

The pseudoaglycone fragment of LL-E33288 lacks a rhamnose derivative and an amino sugar. The loss of the amino sugar results in more than a 100-fold loss of biological activity. Purified pseudoaglycone was added to 73-3I cultures of three blocked mutants, strains DR43, DR46 and DR1316, after 60 hours of cultivation. In each case the blocked mutants were capable of converting pseudoaglycone to LL-E33288 complex, as indicated in FIG. 7. Thus each strain retained the ability to make the amino sugar derivatives and rhamnose derivative, and to bind them to the pseudoaglycone fragment (or a part of the pseudoaglycone). For each mutant, pseudoaglycone bypassed, or overcame, the genetic block.

Protoplasting, Regeneration, and Genetic Transfer

Protoplasting is generally achieved by digesting the cell wall with lysozyme. The addition of glycine to the growth medium often facilitates protoplasting of Actinomycetes, probably due to incorporation of glycine into peptidoglycan of the cell wall. (Examples of protoplasting procedures have been collated in reference [Hopwood, D. A., et. al. 1985. Genetic Manipulation of

*Streptomyces;* A Laboratory Manual. (The John Innes Foundation, Norwich, England.)]

In order to protoplast strain NRRL-15839, 250–500 μl of an overnight of 5x concentrated cells, stored in 20% glycerol at −70° C., were inoculated into 50 ml of GER medium [per 1, 3 g beef extract, 5 g tryptone, 1 g dextrose, 24 g soluble starch and 5 g yeast extract, pH 7.6 (Kim, K. S., and D. Y. Ryu. 1983. Enz. Mic. Technol. 5: 273–280] containing 0.15% glycine and 20 mM CaCl$_2$, at 28° C. Cells were grown for 48 to 60 hours, and the incubation was continued until about 8 hours after the appearance of orange pigment. Since vigorous aeration was found to be essential for good protoplasting, cells were grown in 250 ml baffled flasks on a floor shaker set at 200 rpm. The addition of 3 glass beads (about 4 mm diameter) prevented clumping, and aided in the growth and the protoplasting of cultures.

Cells were harvested by centrifuging at 3200 rpm for 10′. The pellet was washed with 50 ml of 10.3% sucrose and centrifuged again. The pellet was resuspended in 4 ml of protoplasting buffer containing mg/ml lysozyme (either Calbiochem or Sigma). Protoplasting buffer was similar to L buffer [Hopwood, D. A., et. al. 1985. Genetic Manipulation of *Streptomyces;* A Laboratory Manual. (The John Innes Foundation, Norwich, England)], except the pH was 7.6. A modified form of P buffer (Kim, K. S., and D. Y. Ryu. 1983. Enz. Mic. Technol. 5: 273–280) was also employed; MgCl$_2$ was 25 mM and CaCl$_2$ was to 50 mM, and again the pH was 7.6. Cells were incubated for one-two hours at 30° C. The extent of protoplasting was monitored in the phase contrast microscope. Since mycelia may inhibit the regeneration of protoplasts, it was advantageous to wait until the vast majority of the lysozyme-treated culture had protoplasted. We generally observed more than 95% protoplasting; if fewer than 80% of cells were protoplasts, the culture was not used. If the time of protoplasting exceeded 2 hours, we did not observe effective regeneration. In all cases after protoplasting, the final concentration of MgCl$_2$ and CaCl$_2$ was adjusted to 25 mM and 50 mM respectively, and the volume was brought up to 3 ml in our modified P buffer. In order to separate protoplasts from mycelia, to enhance the frequency of regeneration, we filtered through cotton as described [Hopwood, D. A., et. al. 1985. Genetic Manipulation of *Streptomyces;* A Laboratory Manual. (The John Innes Foundation, Norwich, England)], after first rinsing the preparation with modified P buffer. Alternatively we filtered through Schleicher and Schuell Spartan filters with 5 micron pore size, after rinsing with modified P buffer.

Protoplasts were regenerated by inoculating them onto regeneration medium (as described in Kim, K. S., and D. Y. Ryu. 1983. Enz. Mic. Technol. 5: 273–280) except that the optimal concentration of sucrose was found to be 0.15M. The efficiency of regeneration was improved by overlaying protoplasts in soft agar. Protoplasts regenerated to form visible colonies after incubation at 30° C. in 10 days to 2 weeks.

Several modifications of the regeneration conditions were attempted, but without success. Succinate and glycerol were ineffective as osmotic stabilizers, because mycelia could not tolerate them at high concentrations. The presence of alternative carbon sources would probably not alter carbon utilization in regeneration medium, since sucrose, a preferred carbon source, was required as the osmotic stabilizer. Other nitrogen sources, yeast extract at 0.5%, or NZ amine at 0.5%, were substituted for asparagine. We observed only mucoid colonies, albeit at a reasonable frequency, compared to our regeneration medium containing asparagine. The colonies, in the microscope, appeared to contain L forms and not mycelia. Furthermore the colonies would not replicate onto media lacking osmotic stabilizer. Apparently regeneration of protoplasts is enhanced in medium containing a growth-rate limiting nitrogen source. We also attempted to regenerate protoplasts on GER medium containing sucrose as an osmotic stabilizer, and some added minerals. Again mucoid colonies grew up at a reasonable frequency, but they appeared also to be L forms.

The following is a typical successful experiment. Cells were harvested and treated with lysozyme as described above. After 1.5 hours at 30° C., about 95% of cells were protoplasts, estimated by microscopic observation. The concentration of protoplasts was determined to be $2.9 \times 10^9$/ml, using a Petroff-Hauser counting chamber. The culture was gently filtered through a 5 micron filter. Only protoplasts, and about 1% of small mycelial fragments, were observed in the microscope. The titer of protoplasts was $2.35 \times 10^9$/ml. Protoplasts were diluted in modified P buffer and plated on regeneration medium. The culture was also plated on regeneration medium that lacked sucrose, in order to measure cells that hadn't been protoplasted, since protoplasts would lyse in the absence of osmotic stabilizer. After 3 days a few colonies were visible for the less dilute inocula, for plates with or without 0.15M sucrose. These colonies presumably represent cells that were not protoplasted. After 1 week more colonies were visible due to protoplast regeneration. After 11 days almost all the surviving protoplasts formed visible colonies.

| 0.2 M Sucrose | Dilution | Colonies | Colonies/ml | % Survival |
|---|---|---|---|---|
| − | $5 \times 10^{-5}$ | 394 | $8 \times 10^6$ | 0.3% |
| − | $5 \times 10^{-7}$ | 12 | $2 \times 10^7$ | 0.9% |
| + | $5 \times 10^{-5}$ | 3240 | $6.5 \times 10^7$ | 2.8% |
| + | $5 \times 10^{-7}$ | 50 | $1 \times 10^8$ | 4.2% |

The addition of sucrose enhanced survival of the protoplast culture, even though 0.2M sucrose inhibits growth of mycelia. Therefore, the enhanced survival in the medium containing sucrose is due to the regeneration of protoplasts. Our frequency of regeneration of from 1–4% is reasonable for a transformation system.

In order to demonstrate genetic exchange between derivatives of strain NRRL-15839, we attempted a protoplast fusion between two auxotrophs. Strain DR226 requires uracil and arginine for growth, while strain DR146 requires aromatic amino acids, para-amino benzoic acid, and para-hydroxy benzoic acid. Both mutants may contain a single lesion affecting one biochemical reaction (production of carbamoll phosphate for the uracil-arginine requirer, and of shikimic acid pathway for the aromatic amino acid requirer). By fusing protoplasts of the two mutants, we hoped to observe the regeneration of wild type cells.

Cells were protoplasted as described above. 100 μl of DR226 was mixed in a microcentrifuge tube with 100 μl of DR146. After centrifugation for 10 seconds, the supernatant was poured off, and protoplasts were gently resuspended in the remaining drop of supernatant. 0.8 ml of a 50% polyethylene glycol solution (PEG 1000, Baker) was added in modified P buffer as described. In order to select for prototrophs, a minimal regeneration medium lacking 0.01% casamino acids, was used, since the regeneration frequency was found to be about the same with or without casamino acids. 50 µl of fused protoplasts were overlaid onto minimal regeneration agar plates containing no osmotic stabilizer, or 0.2M sucrose. We also plated an equal volume of mycelia before protoplasting as a control. After four weeks the following colonies were observed.

|  | 0 M sucrose | 0.2 M sucrose |
|---|---|---|
| DR146 mycelia | 0 |  |
| DR226 mycelia | 1 |  |
| DR146 and DR226 protoplasts | 1 | 30 |

The number of prototrophs among mycelia is practically 0, whereas after protoplasting the two cultures and fusing, a small but significant number of prototrophs regenerated (the maximum regeneration frequency observed is 4%). The fusion of auxotrophs to prototrophy demonstrates the ability to transfer genes within two derivatives of NRRL-15839. It is now possible to transfer mutations from one strain to another.

Constructing a Plasmid for Transforming Strain NRRL-15839

We did not detect endogenous plasmids within NRRL-15839. *Micromonospora* is related to *Streptomyces*, and several *Streptomyces* plasmids are available. We therefore decided to construct a derivative of a well-characterized plasmid from *Streptomyces*, with the hope that it would also replicate in strain NRRL-15839.

The *Streptomyces* promoter probe plasmid pIJ486 contains the thiostrepton resistance gene on a multicopy plasmid. Since its replicon derives from pIJ101, which has a broad host range within *Streptomyces*, pIJ486 seemed to be a good starting point for a *Micromonospora* plasmid. The thiostrepton resistance gene was not useful, since strain LL-E33288 is partially resistant to at least 500 µg/ml thiostrepton in GER or minimal agar medium. pIJ486, however, also contains another potentially useful gene, the kanamycin resistance gene from the transposon tn5, called aphII. The aphII gene, however, lacks a promotar, and is therefore expressed at very low levels. Promoters can be identified by cloning fragments into a polylinker upstream of the coding region for aphII, transforming *S. lividans*, and selecting or screening for kanamycin resistance. To "activate" the aphII gene, we inserted DNA fragments from strain NRRL-15839 for two reasons. A promoter derived from *Micromonospora* would afford the most chance of driving expression of aphII when the plasmid derivative is transferred from *S. lividans* to strain NRRL-15839. Also, a DNA sequence derived from *Micromonospora* could permit an alternative mode of maintenance of the plasmid derivative, by homologous recombination, if the plasmid replicon failed to function in strain NRRL-15839.

Plasmid was prepared from *S. lividans* TK54/pIJ486 by alkaline lysis with NaCH-SDS, and neutralization with acidic K acetate as described [Hopwood, D. A., et. al. 1985. Genetic Manipulation of *Streptomyces*; A Laboratory Manual. (The John Innes Foundation, Norwich, England.)], and then by CsCl density gradient centrifugation [Maniatis, T., E. F. Fritsch, and J. Sambrook. 1982. Molecular Cloning. (Cold Spring Harbor Laboratory, Cold Spring Harbor, N.Y.)]. The purified plasmid was then digested at the unique BamHI site, extracted with phenol, and precipitated with ammonium acetate and ethanol. The linear plasmid molecule was treated with calf-intestinal alkaline phosphatase to prevent ligation of vector to vector ends. The enzyme was inactivated by heat killing and phenol extraction. After precipitation with acidified Na acetate and ethanol, the vector was resuspended in I.E buffer (10 mM Tris pH 8, 1 mM EDTA), and was ready for ligation. All enzymes were from Boehringer Mannheim, and all reactions were carried out as recommended by Boehringer Mannheim. *Micromonospora* chromosomal DNA was isolated using lysozyme-EDTA, proteinase K, SDS, and phenol-chloroform extraction as described [Hopwood, D. A., et. al. 1985 Genetic Manipulation of *Streptomyces*; A Laboratory Manual. (The John Innes Foundation, Norwich, England.)]. After isopropanol precipitation the DNA preparation was resuspended in 1 ml TE. A streak of the culture revealed that it was pure.

Chromosomal DNA prepared from strain NRRL-15839 was digested with BamHI and Sau3A1, and the fragments were ligated to 0.5 µg of the linearized pIJ486 vector. The molar ratio of insert to vector was 3. After ligating overnight at 16° C. (Boehringer Mannheim enzyme and methods), the DNA was used to transform *S. lividans* strain TK54 as described. For pIJ486 ligated to Sau3A1 inserts, 0.25 µg of ligated DNA was added to protoplasts of TK54, which were inoculated on an R5 plate and incubated for 30 hours at 28° C. The plate was overlayed with 1/10 volume of R5 soft agar containing 100 µg/ml of kanamycin. For pIJ486 ligated to BamHI inserts, 0.5 µg of ligated DNA was added to protoplasts of TK54, and aliquots were inoculated onto two plates. One was overlayed with kanamycin as indicated, and the other with 500 µg/ml thiostrepton in the overlay. For the latter plate, 71 colonies grew following addition of thiostrepton. For the plates overlaid with kanamycin, a lawn of cells grew on much of the plate. From patches of plates, single colonies were isolated. We observed the following results when colonies were replicated onto minimal medium containing the drug indicated.

| Ligation and Selection | # of Colonies Replicated | Number of Resistant Colonies | | | Clones |
|---|---|---|---|---|---|
|  |  | 50 micro g/ml thiostrepton | 2 micro g/ml kanamycin | 20 micro g/ml kanamycin |  |
| Transformation A BamHI fragments selected with thiostrepton | 56 | 54 | 37 | 17 | pPP4 |
| Transformation B BamHI fragments selected with kanamycin | 100 | 5 | 28 | 9 | pPP8 |
| Transformation C Sau3A1 fragments | 100 | 43 | 45 | 6 | pPP14 |

| | # of | Number of Resistant Colonies | | | |
|---|---|---|---|---|---|
| Ligation and Selection | Colonies Replicated | 50 micro g/ml thiostrepton | 2 micro g/ml kanamycin | 20 micro g/ml kanamycin | Clones |
| selected with kanamycin | | | | | |

Many of the clones selected directly with kanamycin were artifacts. In transformation A, only 5 colonies were resistant to thiostrepton. We assumed that thiostrepton-sensitive clones were not true transformants. Transformation B was more effective Among 45 putative kanamycin resistant transformants, 43 were also resistant to thiostrepton. Of the 56 clones selected with thiostrepton (transformation C), 54 proved to be thiostrepton resistant when retested, and of those, 34 were at least marginally kanamycin resistant, suggesting that most inserts containei promoters directing expression of aphII.

To show that clones resistant to kanamycin and thiostrepton contained plasmid, we isolated plasmid from 17 clones that were the most kanamycin resistant, judging by colony size on plates containing 20 μg/ml kanamycin. Ten were from transformation A, 1 from transformation B, and 6 from transformation C. Plasmid minipreps were prepared as outlined above for plasmid preparations, except that minipreps were scaled down as described. Plasmids were observed in each preparation by agarose gel electrophoresis. At least 14 of the clones contained plasmid larger than the pIJ486 control, suggesting that kanamycin resistance was due to a *Micromonospora* DNA insert in front of the aphII gene. The insert size was determined for 5 clones by restriction analysis to be 8.5 Kbp (plasmid pPP4), 1.8 Kbp (plasmid pPP8), 0.7 Kbp, 0.7 Kbp, and 0.4 Kbp (plasmid pPP14). The 3 clones that were most resistant to kanamycin, carrying plasmids pPP4, pPP8, and pPP14, grew on R5 agar medium containing 200 μg/ml kanamycin and 50 μg/ml thiostrepton, and on minimal plates containing 20 μg/ml kanamycin.

The presence of *Micromonospora* inserts in these three plasmids was confirmed by Southern analysis, as in Schleicher and Schuell (FIG. 8). *Micromonospora* DNA and *S. lividans* TK54 chromosomal DNA was digested with BamHI, applied to a 0.7% agarose gel, and denatured in alkali. DNA was transferred to a nitrocellulose filter, which was hybridized with probe of purified pPP8 DNA (0.5 μg) labeled with $\alpha-{}^{32}P$-dCTP by nick translation (NEN nick translation kit). About $10^6$ cpm of probe was hybridized with the filter at 42° C. The final wash was at 55° C. at 0.1×SSC. Lane one is a control showing the hybridization of probe to 150 ng of pPP8, restricted with BamHI. The probe hybridizes to two bands; the 1.8 Kbp insert band, and the larger band representing linear pIJ486, which is 6.2 Kbp. In lane 2, 2.5 μg of *Micromonospora* DNA, restricted with BamHI, was applied. The 1.8 Kbp band is clearly visible, indicating its presence in the *Micromonospora* chromosome. Lane 3, containing *S. lividans* DNA, gives no signal, indicating that the 1.8 Kbp is not derived from the *S. lividans* genome. Similar experiments were performed using pPP4. Two BamHI bands were observed when the probe was hybridized to *Micromonospora* DNA digested with BamHI, and no bands with *S. lividans* DNA, indicating that pPP4 contains two BamHI fragments from *Micromonospora* that add up to 8.5 Kbp. When pPP14 was used as probe, again a band was observed only when *Micromonospora* DNA, cut with BamHI, was probed, and not *S. lividans* DNA. In all three cases, therefore, the DNA inserts, activating expression of the aphII gene, were derived from strain NRRL-15839.

Plasmids pPP4, pPP8 and pPP14 were placed in host *S. lividans* TK54 and deposited with the American Type Culture Collection, 12301 Parklawn Drive, Rockville, Md. 20852 on Mar. 6, 1987, and have been added to its permanent collection. pPP4 has been assigned by such depository the strain designation the strain designation ATCC- 67,343, pPP8 has been assigned by such depository the strain designation AICC-67342, and pPP14 has been assigned by such depository the strain designation ATCC-67341. Access to such cultures, during the pendency of the instant application, shall te available to one determined by the Commissioner of Patents and Trademarks to be entitled thereto under 37 C.F.R. §1.14 and 35 U.S.C. §122, and all restrictions on availability to the public of such cultures will be irrevocably removed upon grant of a patent on the instant application.

Transformation of Strain LL-E33288

Plasmid pPP8 was used to transform protoplasts of NRRL-15839, since it conferred resistance to kanamycin and contained a sizable insert (1.8 Kbp). Our rationale was the following. If the replicon of pIJ486 failed to replicate in strain NRRL-15839, then the plasmid could still be maintained by homologous recombination into the *Micromonospora* chromosome. A plasmid with a smaller insert (i.e. pPP14) is less likely to undergo recombination. Plasmid pPP4 seemed a less attractive choice since its insert (8.5 Kbp) dramatically increased the size of the plasmid. If *Micromonospora* contains a restriction system capable of digesting unmodified foreign DNA, then it would probably restrict such a large plasmid more severely than pPP8.

Protoplasts of strain NRRL-15839 were prepared as previously described above, using 5 micron filters following lysozyme treatment. Protoplasts were transformed with pPP8 plasmid DNA, using the protocol similar to that used for *Streptomyces* transformations [Hopwood, D. A., et. al. 1985. Genetic Manipulation of *Streptomyces*; A Laboratory Manual. (The John Innes Foundation, Norwich, England.)]. 100 μl, containing $3.4\times10^8$ protoplasts, was centrifuged for 10 seconds (microcentrifuge), the pellet was decanted, and protoplasts were carefully resuspended in the remaining drop of supernatant. 18 μl of pPP8 (4 μg) was added, and then 100 μl of 25% PEG 1000 in T buffer was added. Controls were plated to indicate the regeneration frequency, and most of the transformation mix was overlayed onto 4 RM plates that had 0.15M sucrose.

Transformants were selected by overlaying the plates with 150 μg/ml of kanamycin in 1/10 volume of soft agar. It was not clear, however, wher to add the drug. Transformants might not survive if kanamycin were added too early, before drug resistance was well expressed, and/or before fragile protoplasts began to regenerate. If kanamycin were added after the optimal time, then transformants might not be detected if the plasmid were not stably maintained in strain NRRL-15839, or if mycelia inhibited the regeneration of protoplasts. We therefore decided to add the kanamycin overlay at two times; after one day of incubation at 28° C., and after 6 days. Six colonies grew from plates overlaid after 1 day and 127 colonies when plates were overlaid after 6 days. Colonies were replicated on GER plates containing no kanamycin, or 1 or 5 μg/ml kanamycin. The 17 colonies that grew well in the presence of kanamycin were retested on plates with 50, 15 and 5 μg/ml of drug, and their resistance to kanamycin suggested that they might contain plasmid. Furthermore, these 17 colonies appeared to be slightly more resistant to thiostrepton (500 μg/ml in GER plates); kanamycin-resistant clones grew up in the presence of thiostrepton one day before the wild type colonies.

Plasmid minipreps were made for six clones that grew in the presence of 50 μg/ml kanamycin, from GER plate cultures containing 5 μg/ml kanamycin. Ten μl of a 25 μl plasmid preparation was applied to a 0.7% agarose gel. Though the chromosomal band in our minipreps was prominent, it was difficult to tell whether a plasmid band was present. It was conceivable that the plasmid pPP8 was present in our kanamycin resistant strains, but at a lower copy number than in *S. lividans*. It was also possible that plasmid sequences were maintained after integration into the bacterial chromosome. In order to increase our detection capabilities, and to distinguish between these two possibilities, a Southern transfer was performed (Schleicher and Schuell method) and the parent plasmid, pIJ486, was used as probe.

Figure 9:
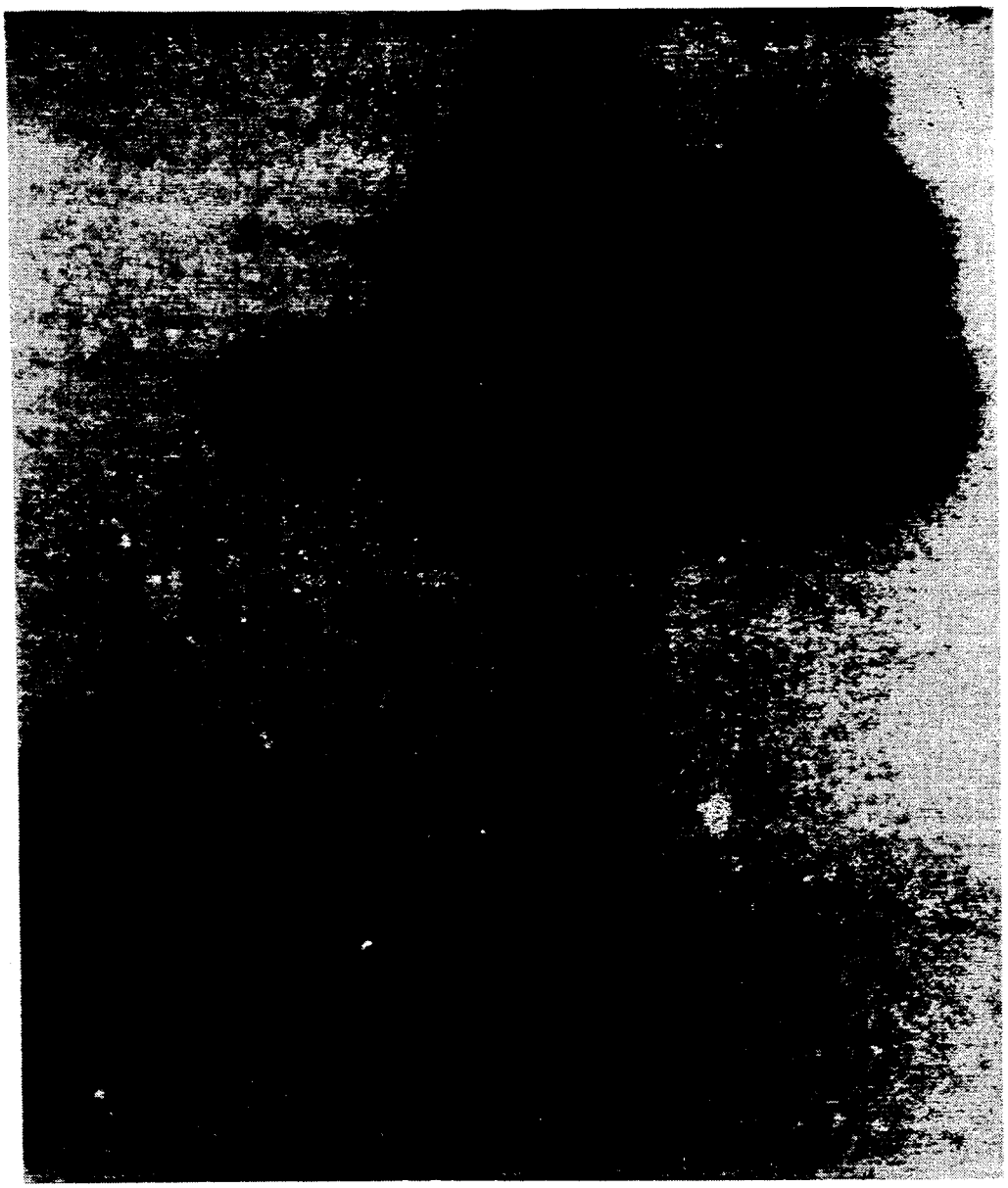
FIG. 9 shows detection of autonomous plasmid pPP8 in a kanamycin-resistant transformant of NRRL-15839 by Southern hybridization, with the following legend: Lane 1, plasmid miniprep DNA of the kanamycin resistant transformant; Lane 2 plasmid miniprep pPP8 from *S. lividans;* and Lane 3 CsCl purified plasmid prep pPP8 from *S. lividans,* plasmid DNA being detected following agarose gel electrophoresis (0.7%, TBE) by hybridizing with labeled plasmid pIJ486.

The Southern hybridization is shown in FIG. 9. Lanes 1 and 2 contain pPP8 purified plasmid and a miniprep of *S. lividans* strain TK54/pPP8 DNA fixed to the filter; there are two DNA bands that hybridize to the probe, corresponding to the covalently closed circular and nicked plasmid forms. An inspection of the stained gel, prior to transfer, indicated the position of the chromosomal DNA band, which was clearly above the supercoiled plasmid band. In lane 3, the prominent signal from one putative *Micromonospora* transformant is in the same position as covalently closed circles of pPP8 from *S. lividans*. Thus pPP8 replicates autonomously in strain NRRL-15839, and is not integrated.

Figure 10:
FIG. 10 shows detection of plasmid sequences in the kanamycin-resistant transformant of strain NRRL- 15839, after digestion with BamHI restriction enzyme, in that DNA samples were restricted with BamHI and hybridized with labeled plasmid pIJ486 following agarose gel electrophoresis (0.7%, TBE), with the following legend: Lane 1, DNA from kanamycin resistant transformant strain NRRL-15839; Lane 2, DNA of strain NRRL-15839; and Lane 3, DNA of *S. lividans* TK54/pPP8.

The miniprep of the *Micromonospora* plasmid was also restricted with BamHI, which should release the 1.8 Kbp insert from the plasmid, resulting in a linear form of pIJ486. A Southern of that gel is shown in FIG. 10. Lane 1 shows a purified plasmid preparation of pPP8 cut with BamHI, and probed with labeled pIJ486. Lane 2 shows no signal when DNA from strain NRRL-15839 is run in the gel. In lane 3 DNA from the *Micromonospora* miniprep was cut with BamHI before gel electrophoresis. The probe hyridized with a band corresponding to pIJ486, confirming the presence of plasmid in the transformant.

Another plasmid miniprep from the *Micromonospora* transformant was used to transform *S. lividans* TK54 protoplasts to thiostrepton resistance. Three thiostrepton resistant colonies were obtained. Plasmid was prepared from one clone, and agarose gel electrophoresis revealed a plasmid of the size of pPP8. The recovery of a plasmid from *Micromonospora* that confers thiostrepton and kanamycin resistance confirms independently that we isolated a *Micromonospora* transformant.

Characterization of a DNA Sequence Promoting Transcription in the Stationary Phase, Concurrent with LL-E33288 Production Our original goal was to define the promoters discussed above that were derived from *Micromonospora*, and to show whether initiation sites used by strain NRRL-15839 were similar to those of *Streptomyces lividans*, a relatively well-characterized organism. It became increasingly evident that we had one DNA sequence from *Micromonospora* that had unexpected and potentially very useful properties. This DNA fragment contains multiple promoters of two types. One promoter is active predominantly in growing cells, an activity that was selected for by demanding kanamycin resistance. In addition the fragment contains a cluster of 3 promoters which are most active when cells have entered stationary phase and the drug LL-E33288 complex is produced. We now have the capacity to regulate the expression of genes so that they will be expressed at a particular time of the life cycle, by juxtaposing a given structural gene downstream of the promoter-bearing fragment, or a smaller derivative of it. It may be advantageous to express certain genes only during stationary phase, since it may be lethal if some genes are expressed during the exponential phase. A structural gere, for example, coding for an enzyme that is part of the LL-E33288 complex biosynthetic pathway could be placed after our DNA sequence, so that the enzyme activity would only appear when drug is made. A detailed analysis of promoters from *Micromonospora* contained on plasmid pPP14 is described below.

Figure 8:
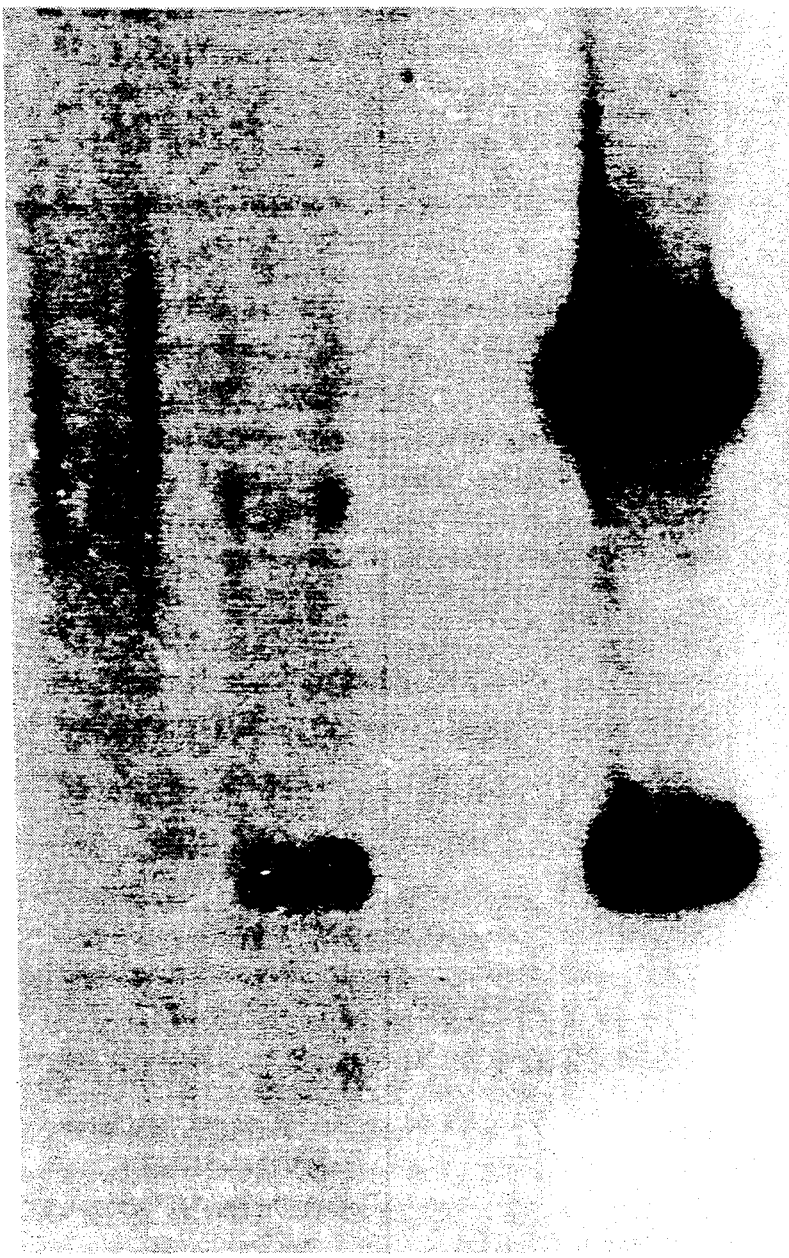
FIG. 8 shows detection of *Micromonospora* inserts by Southern hybridization, in that following agarose gel electrophoresis (0.8%, TBE buffer) the following samples were fixed on a nitrocellulose filter and probed with labeled plasmid pPP8, with the following legend: Lane 1, *S. lividans* chromosomal DNA digested with BamHI; Lane 2, LL-E33288 chromosomal DNA digested with BamHI; Lane 3, pPP8 digested with BamHI; the Southern blot being probed with pPP8 and showing that 1.8 Kbp insert is from NRRL-15839 DNA.

Southern analysis had shown that plasmids pPP4, pPP8 and pPP14 all contained DNA derived from strain NRRL-15839 inserted in front of the aphII gene (FIG. 8). Since the DNA sequences promote expression of the aphII gene in *S. lividans*, we decided to examine their promoter activity in *Micromonospora*, by isolating RNA from strain NRRL-15839 and measuring transcription.

A frozen seed culture of cells was inoculated into 50 ml of GER medium (3/100 dilution) and after 60 hours incubation, the culture was mixed with frozen medium and centrifuged for 3' at 10000 rpm, and the cell pellet was stored at −70° C. until used. To prevent degradation of RNA, the cells were rapidly harvested and quick-cooled. Pellets were resuspended in guanidinium isothiocyanate solution (Chirgwin, J. M., et. al. 1979. Biochem. 18: 5294–5299), and sonicated for a total of 1–2', at 16 micron power in the Soniprep 150 (MSE); at least 90% of cells were lysed by microscopic observation. RNA was isolated by centrifuging through a CsCl cushion (Turpen, T. H., and O. M. Griffith. 1986. Biotechniques 4: 11–15), extracted with phenol-chloroform, ethanol precipitated, and stored as an ethanol precipitate at −20° C., or in water at −70° C. To identify the endogenous transcripts coded by the inserts of pPP4, pPP8 and pPP14, the RNA from strain NRRL-15839 was applied to an agarose gel containing formaldehyde [Maniatis, T., E. F. Fritsch, and J. Sambrook. 1982. Molecular Cloning. (Cold Spring Harbor Laboratory, Cold Spring Harbor, N.Y.)], transferred to a filter, and hybridized to labeled pPP4, pPP8 or pPP14 (Northern analysis).

Figure 11:
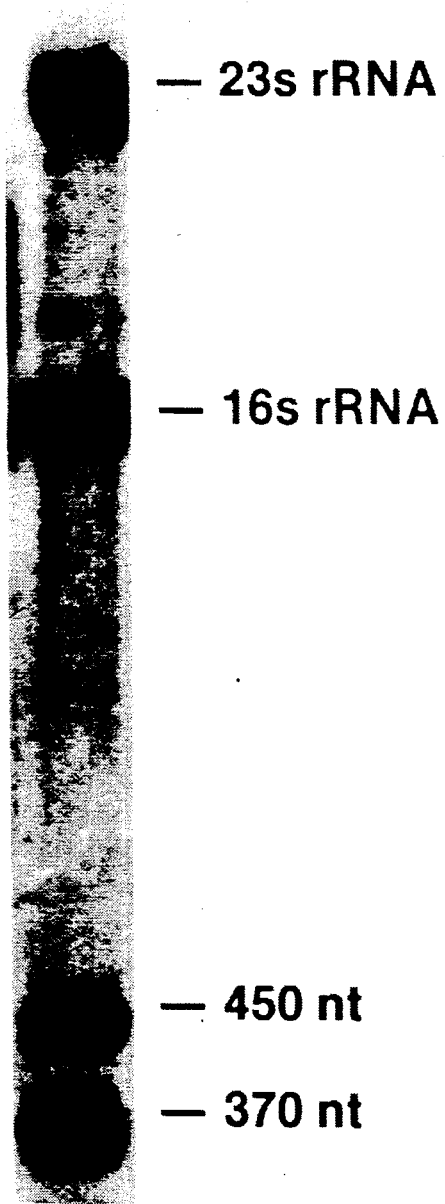
FIG. 11 shows Northern analysis of RNA isolated from *Micromonospora* strain NRRL-15839, in that total RNA was isolated from *Micromonospora* grown in GER medium for 60 hours as described in the text, 10 μg of RNA were electrophoresed in a formaldehyde-agarose gel, transferred to nitrocellulose and probed with nick-translated pPP14, two major transcripts, 450 nt and 370 nt, are detected, and, in addition, background hybridization to ribosomal RNAs is observed.

FIG. 11 is the first Northern experiment. Two transcripts, 450 and 375 bases long, hybridize to the pPP14 probe. Because pPP14 hybridized to two distinct transcripts, it appeared that at least two signals involved in the regulation of transcription were within the *Micromonospora* DNA insert. The fragment could contain two or more promoters (sites essential for initiation of transcription), or a promoter and a transcription-termination site.

In order to precisely identify transcription initiation sites within the 0.4 kbp *Micromonospora* DNA insert, we next began a series of S1 nuclease transcriptional mapping studies. The 0.4 kbp insert was subcloned into pUC19, an *E. coli* vector, by utilizing the HindIII site of the polylinker, and the BamHI site proximal to aphII, and transforming *E. coli* strain JM83 (New England Biolabs) to ampicillin resistance. (One BamHI site was recreated when the Sau3A1 fragment was ligated into the BamHI site of pIJ486.) The resulting plasmid, designated pPEC14, was used for subsequent labeling experiments. The fragment was labeled by kinasing the BamHI site (Boehringer Mannheim enzyme and reaction conditions), and digested with HindIII enzyme, and single-stranded probe was isolated [Maniatis, T., E. F. Fritsch, and J. Sambrook. 1982. Molecular Cloning. (Cold Spring Harbor Laboratory, Cold Spring Harbor, N.Y.)]. Excess of the probe was hybridized with 10 μg of RNA from strain NRRL-15839 or from *S. lividans* TK54/pPP14, and the hybridized samples were treated with S1 nuclease at a final concentration of 300 units/ml (Boehringer Mannheim), as outlined (Brosius, J., R. L. Cate, R. Perlmutter. 1982. J. Biol. Chem. 257: 9205–9210). After ethanol precipitation, samples were analyzed by gel electrophoresis and autoradiography.

Figure 12:
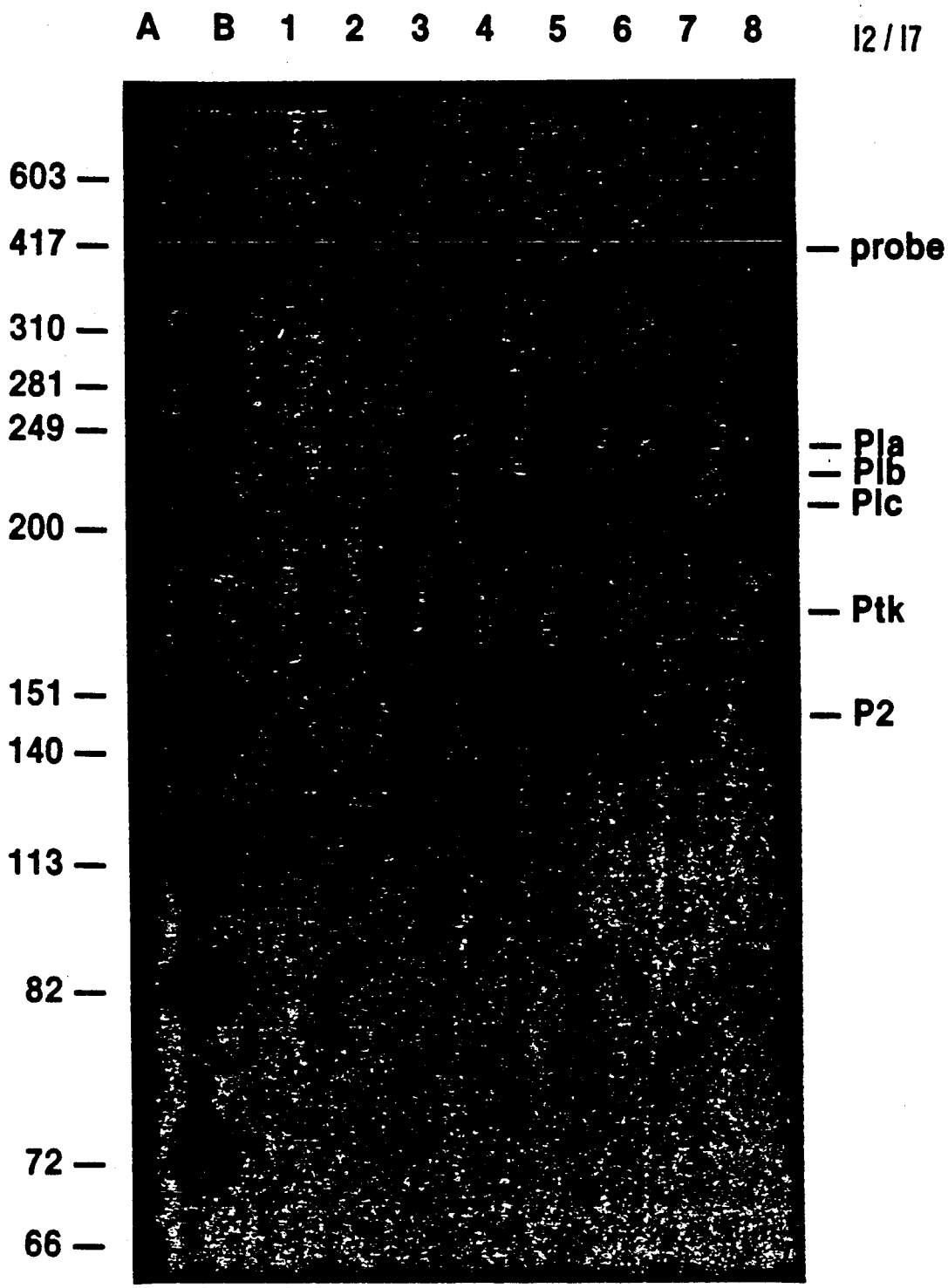
FIG. 12 shows mapping transcriptional start sites in pPP14 by S1 nuclease protection, in that RNA was hybridized to a single-stranded probe from pPEC14 labeled at the BamHI site, and samples were digested with S1 nuclease prior to electrophoresis on an 8% acrylamide/7M urea sequencing gel, with the following legend: Lane 1, undigested probe; Lane 2 no RNA; Lanes 3, 4, 5: 1, 3 and 10 μg respectively of *Micromonospora* RNA; Lanes 6, 7, 8: 10 μg of RNA isolated from *Streptomyces lividans* TK54 untransformed, or transformed with pIJ486 or pPP14; and Lanes A and B are molecular weight markers of phi-x 174 DNA cut with HaeIII or HinfI.

FIG. 12 shows that RNA from the GER culture of strain NRRL-15839, hybridizes and protects the probe from S1 nuclease digestion. Four apparent start sites were detected; one start site approximately 150 bp from the BamHI end, and a cluster of 3 start sites about 225 bp from the BamHI end. Apparently there are multiple start sites for transcription in the same direction within this *Micromonospora* DNA fragment. RNA was also prepared from a GER culture of *S. lividans* TK54/pPP14 and hybridized to the probe, ani S1 transcriptional mapping analysis indicated that the start sites were the same in the two species. One additional start site apparently occurs in *S. lividans* that is not detectable in *Micromonospora*, about 170 bp from the BamHI site. Because the pattern of transcription was so similar in the two species, the approach of selecting for promoter activity in *S. lividans* is valid.

Figure 13:
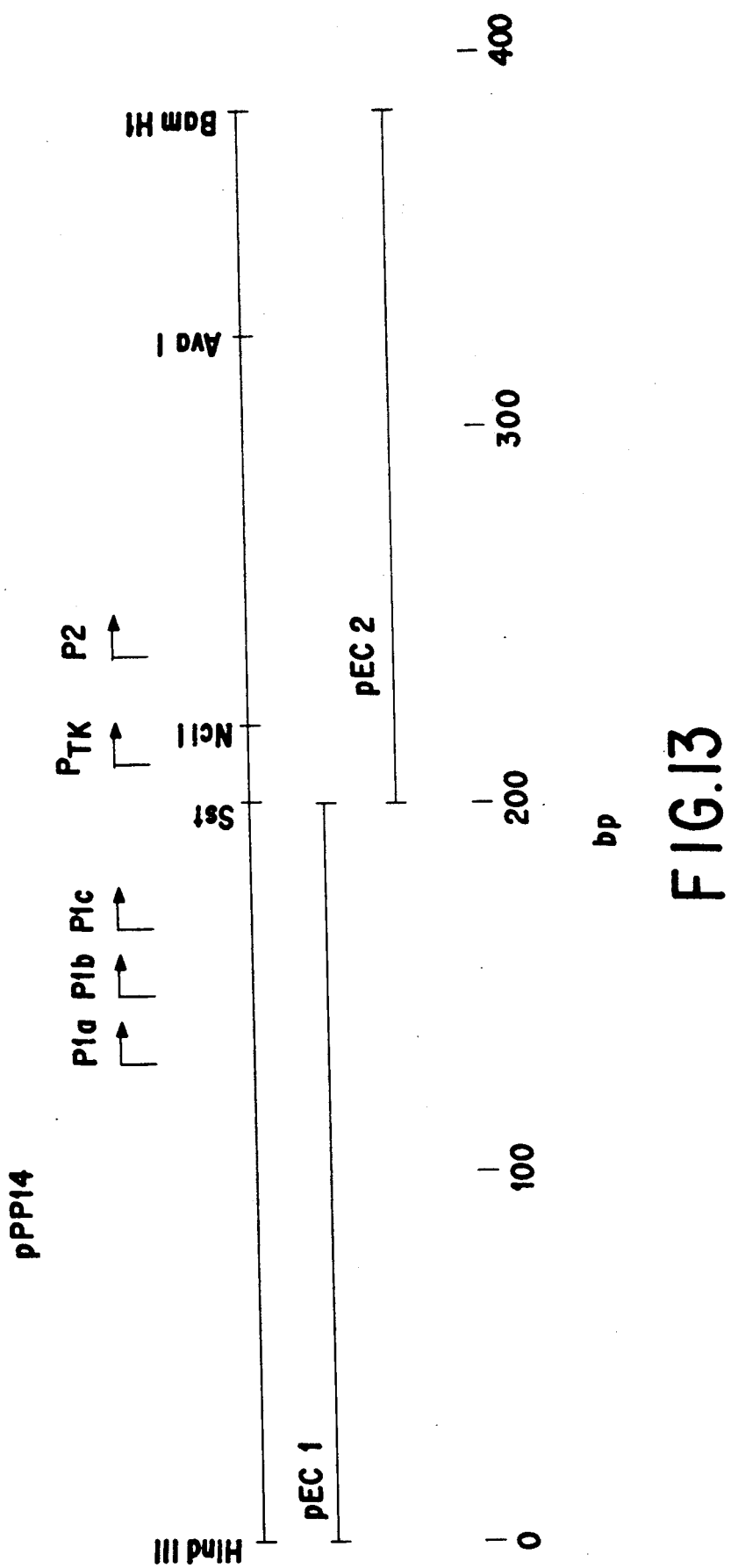
FIG. 13 shows restriction map of *Micromonospora* DNA insert contained in pPP14, the location of transcriptional start sites determined by S1 nuclease protection.

A map of the 0.4 kbp fragment, showing the transcription start sites as well as useful restriction sites is shown in FIG. 13. The spacing between the downstream promoter (designated P2) and the 3 upstream promoters (designated P1a, P1b and P1c) was about the same as the spacing between the RNAs observed with the Northern analysis (FIG. 11). Thus, it seemed likely that the 0.4kbp fragment contained several initiation sites for transcripts that had a common 3' end. We found no detectable transcript when the other strand was labeled and hybridized with *S. lividans* RNA, indicating no promoter activity in the diverging direction.

To correlate transcription from P1 and P2 with the two bands observed by Northern analysis, the following experiment was performed. Derivatives of the pPEC14 plasmid were constructed that contained a subfragment of the 0.4 kbp sequence into pUC19, by utilizing the SstII site in the middle of the 0.4 Kbp insert. The upstream portion (containing the P1 cluster) was deleted by digesting with PstI and SstII, blunting with T4 DNA polymerase (Boehringer Mannheim) [Maniatis, T., E. F. Fritsch, and J. Sambrook. 1982. Molecular Cloning. (Cold Spring Harbor Laboratory, Cold Spring Harbor, N.Y.)], and ligating to form pPEC2. The downstream portion of the 0.4 kbp fragment (containing P2) was deleted by digesting pEC14 with SstII and SmaI, and then blunting and ligating to form pPEC1 (FIG. 13). The prediction was that pPEC1, containing P1, should hybridize with only the larger transcript in a Northern. pPEC2, containing P2, should hybridize to both transcripts. If the two transcripts were not overlapping then pPEC1 and pPEC2 would each hybridize to only one band. In fact, labeled pEC2 hybridized to both transcripts, and labeled pPEC1 to just the larger transcript when the Northern was performed. Thus all the data is consistent with overlapping transcripts.

Figure 14:
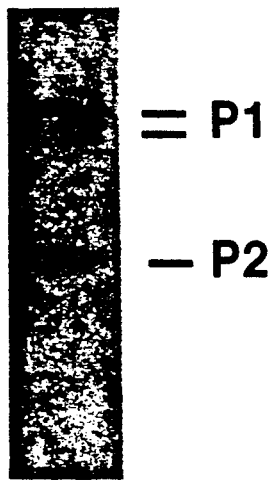
FIG. 14 shows high-resolution Northern analysis of transcripts hybridizing to pPEC14, in that *Micromonospora*P RNA (10 μg) was fractionated on a 5% acrylamide/0.27% bisacrylamide gel containing 7M urea, and the gel was transferred to a Gene Screen Plus membrane (New England Nuclear) by electroblotting as recommended by the manufacturer.

A high-resolution Northern experiment was done in order to see if the larger transcript actually contains multiple bands in the RNA preparation, consistent with initiation from P1a, P1b and P1c. The RNA sample from *Micromonospora* was applied to a 5% acrylamide/0.27% bis gel containing 7M urea. After electrophoresis, the RNA was electroblotted onto nitrocellulose, and probed with labeled pPP14 DNA. FIG. 14 shows that the larger transcript hybridizirg to probe pPP14 can be resolved into more than one component. Since multiple large transcripts are detectable in the RNA preparation, the multiple promoters, P1a, P1b and P1c do not appear to be artifacts of S1 nuclease digestion.

In order to delineate precisely tha locations of the start sites for P1a, P1b, P1c and P2, DNA was sequenced from the AvaI site, downstream of P2, by the Maxam-Gilbert method (Maxam, A. M., and W. Gilbert. 1980. Methods Enzymol. 65: 499–560). For analysis of P1, DNA was sequenced from the HpaII/NciI site. DNA was labeled by kinasing, for the non-coding strand, and by filling in with DNA polymerase Kleno fragment (Boehringer Mannheim enzyme and reaction conditions) for the coding strand. The P1 and P2 start sites were defined by lining up the fragment protected from S1 digestion with a sequencing gel (FIG. 15). Parts of the sequence of the 0.4 kbp fragment were determined by Sanger sequencing (IBI Kit) of plasmids pEC1 and pEC2.

Since multiple promoters were used to transcribe the same downstream RNA, we decided to examine whether differential utilization of these promoters occurred at distinct phases of the growth cycle of *Micromonospora*. Strain NRRL-15839 was grown up in 73-3I medium containing added phosphate ($K_2HPO_4$ to 0.05%), and growth was monitored by a DNA assay using Hoechst 33258 reagent (Calbiochem) as described (McCoy, KW. F., and LB. H. Olson. 1985. Appl. Environ. Microbiol. 49: 811–817). (Similar growth curves were obtained by measuring protein, utilizing the BIO-RAD TM assay.) A culture of strain NRRL-15839 was also grown in a minimal production medium which we developed (Aux, except $K_2HPO_4$ was to 0.05%, KI was added to 0.01%, and the pH of the TES buffer solution was 7.0).

Figure 16:
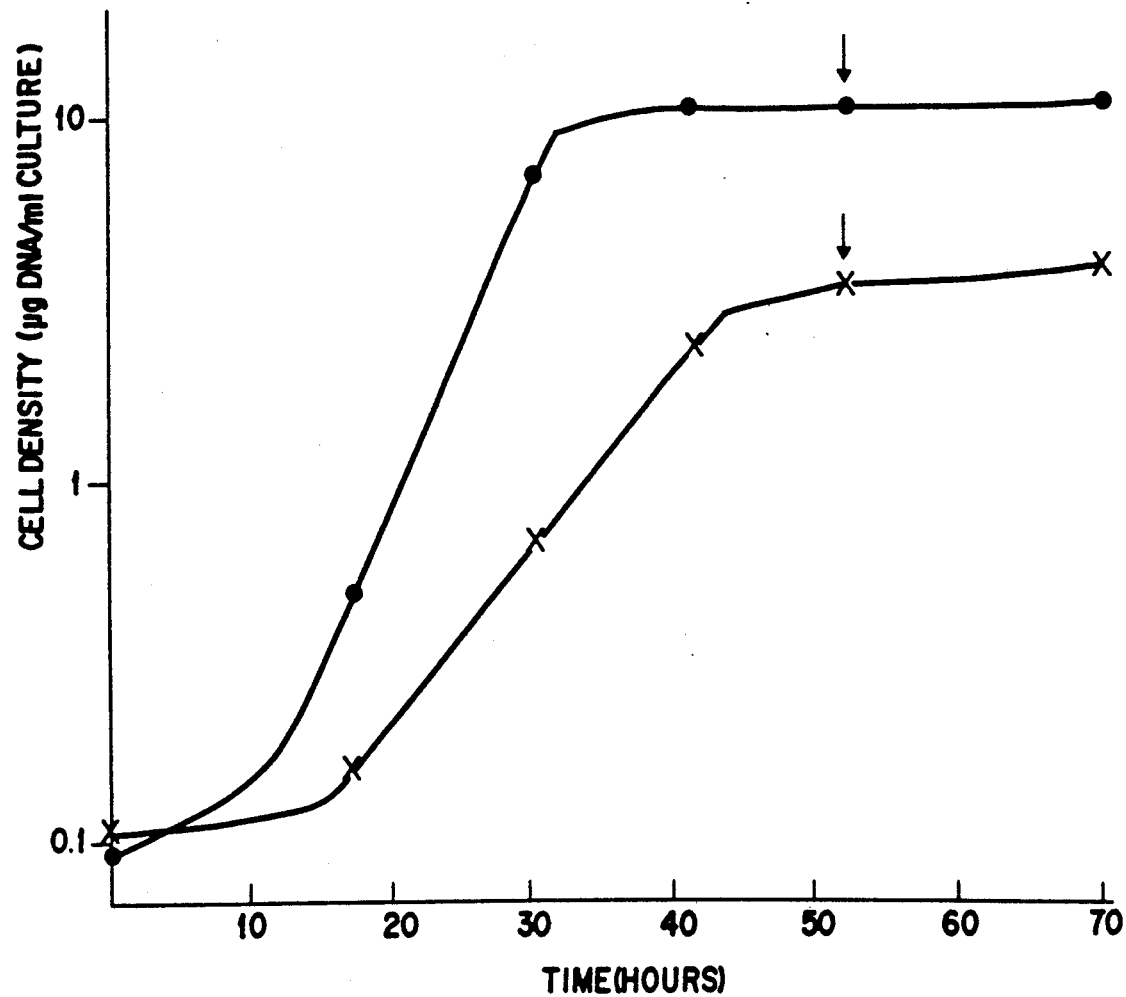
FIG. 16 shows growth curves of strain NRRL-15839 and appearance of LL-E33288 complex, in that cell mass was measured by assaying for the accumulation of DNA in cultures of strain NRRL-15839 grown in 73-3I medium (●), or minimal production medium (X), the arrows indicating the first appearance of LL-E33288 complex.

Growth curves of the culture are shown in FIG. 16. As indicated in the figure, BIA activity was not detected until at least 6 hours after the end of the exponential growing phase. The Northern analysis of RNA for these time points, using labeled pPEC14 as probe, is shown in FIG. 17. The first lane contains RNA isolated from exponentially growing cells; very little of the larger transcripts starting from P1 was detected, and little of the 375 base transcript, from P2. As cells were harvested progressively later in stationary phase, the larger transcripts from P1 became considerably more prominent, whereas the 375 base transcript from P2 diminished slightly (lanes 2–5). Interestingly, the prominence of transcripts originating from P1 parallels the appearance of LL-E33288 complex in the growth medium. We have observed substantially the same results using staged RNA from cells growing in minimal production medium (FIG. 17), or from S1 nuclease transcriptional mapping studies of staged RNAs. We estimate there is at least a ten-fold increase in expression originating from P1 during stationary phase, compared to exponential phase.

The P2 promoter also appears to be subject to regulation. When cells of strain NRR-15839 were grown in GER medium, expression of P2 was more pronounced during exponential phase than for cells grown in either 73–3I, or in minimal production medium (data not shown). During stationary phase in GER medium, transcription from P2 increased, whereas transcription from P2 diminished for cells grown in produrtion media (FIG. 17). The rich nitrogen-containing supplements in GER, compared to production media, may account for these differences in expression from P2 in strain NRRL-15839.

Since the P2 promoter contributes significantly to transcription only during exponential phase for strain NRRL-15839 growing in these production media, we decided to construct plasmids that contained only P1 or only P2. Plasmid pPEC1 was digested with HindIII and EcoRI, and the fragment containing P1a, P1b and P1c was inserted into pIJ486, the promoter-probe plasmid from *Streptomyces*, using its HindIII and EcoRI sites, this plasmid being designated pSL1. Similarly, a fragment containing P2 was obtained by cutting pPEC2 with BamHI and HindIII, and ligating into the BamHI and HindIII sites of pIJ486, this plasmid being designated pSL2. By making these constructs we coud independently assess promoter activity from P1 and from P2. We found that insertion of either sub-fragment in front of the aphII gene confers kanamycin resistance (up to 40 μg/ml on RM plates) to the *S. lividans* TK54 host. S1 transcriptional mapping analysis indicates that the start site of P2 in this construct is identical to the P2 start site of pPP14.

The fact that the insert containing only P2 has significant promoter activity eliminates the possibility that the shorter transcript results from processing of a transcript originating from P1. The promoter activity of P1 in the absence of P2 will be determined to see if the induction during stationary phase is still 10 fold. The data indicate that in strain NRRL-15839, and in transformants of *S. lividans*, the P1 promoters are temporally regulated.

Construction and screenino of strain NRRL-15839 genomic DNA library in *E. coli*

We have constructed two genomic libraries of NRRL-15839 DNA in *E. coli*. Genomic DNA was prepared from strain NRRL-15839 and partially digested with Sau3AI restriction endonuclease (Boehringer Mannheim). he digested DNA was size fractionated in order to maximize for large inserts in cloning (>10 kb). DNA fractionated by sucrose gradient centrifugation was ligated into the BamHI site of plasmid pBR322 (New England Biolabs), and was used to transform *E. coli* strain K802 (New England Biolabs) to ampicillin resistance. The choice of the *E. coli* host strain was found to be critical to ensure high frequency of transformation. Three thousand recombinant clones were obtained, with an average insert size of 14 kbp.

Alternatively, DNA from strain NRRL-15839 was size fractionated by agarose gel electrophoresis, and this DNA was ligated into the BglII site of a derivative of plasmid pKK233-2 (Pharmacia), which we modified by insertion of a polylinker. This vector contains the inducible trc promoter and allows expression of *Micromonospora* DNA in *E. coli*. Approximately 3000 clones containing plasmids with an average insert size 10 kb were obtained.

Hybridization of *Micromonospora* DNA to Polyketide Probes

DNA of strain NRRL-15839 was isolated, digested with BamHI restriction enzyme, and fractionated on an agarose gel for Southern hybridization analysis. The polyketide probes, PIJ2345 and pIJ2346, derived from the act I and act III genes of *S. coelicolor* A3(2) (F. Malpartida et al., 1986 Molecular and General Genetics, Vol. 205, pp. 66–73), were labeled by nick-translation. A BamHI fragment of about 2.5 kbp cross-hybridized with the act I probe.

Physioloqical Studies

The development of a defined redium that supports the production of LL-E33288 complex, provides the opportunity to study the physiogiral factors affecting drug production. The favored carbon source for growth of strain NRRL-15839 is sucrose or glucose. The favored nitrogen source is ammonium. When the minimal medium is changed, and contains alternative carbon and nitrogen sources, the production of drug was observed. When the concentration of axmonium, in particular, was low, then more drug was produced per cell mass. Glutamate (to 1%) was the better nitrogen source for drug production when compared to ammonium, proline, or arginine. Therefore, the nature of the nitrogen source may play an important role in the production of LL-E33288 complex. The nature of the carbon source was less important.

The inventors would like to acknowledge S. Lucania (E. J. Squibb, New Brunswick, N.J.) for providing thiostrepton.

What is claimed is:

1. A culture comprising the microorganism *Micromonospora echinospora* ssp. calichensis DR 46 (ATCC-53591), said culture being capable of producing complementing factor in recoverable quantity upon aerobic fermentation in an aqueous medium containing assimilable sources of carbon, nitrogen, iodine and inorganic salts.

* * * * *